United States Patent
John

(10) Patent No.: US 6,463,328 B1
(45) Date of Patent: Oct. 8, 2002

(54) ADAPTIVE BRAIN STIMULATION METHOD AND SYSTEM

(76) Inventor: Michael Sasha John, 1010 Orienta Ave., Mamaroneck, NY (US) 10543

( * ) Notice: Subject to any disclaimer, the term of this patent is extended or adjusted under 35 U.S.C. 154(b) by 0 days.

(21) Appl. No.: 09/480,052

(22) Filed: Jan. 10, 2000

Related U.S. Application Data

(63) Continuation-in-part of application No. 08/596,450, filed on Feb. 2, 1996, now Pat. No. 6,066,163.

(51) Int. Cl.$^7$ .............. A61N 1/36; A61N 1/18

(52) U.S. Cl. ...................................... 607/45

(58) Field of Search ............................ 607/45, 53, 55, 607/58

(56) References Cited

U.S. PATENT DOCUMENTS

| | | | |
|---|---|---|---|
| 3,850,161 | * 11/1974 | Liss | 607/45 |
| 4,279,258 | 7/1981 | John | 600/544 |
| 4,592,359 | 6/1986 | Galbraith | 607/57 |
| 4,702,254 | 10/1987 | Zabara | 607/45 |
| 4,735,204 | 4/1988 | Sussman et al. | 607/60 |
| 4,846,190 | 7/1989 | John | 600/544 |
| 4,913,160 | 4/1990 | John | 600/544 |
| 5,083,571 | 1/1992 | Prichep | 600/544 |
| 5,287,859 | 2/1994 | John | 600/544 |
| 5,342,409 | 8/1994 | Mullett | 607/46 |
| 5,611,350 | * 3/1997 | John | 600/378 |
| 5,716,377 | 2/1998 | Rise et al. | 607/2 |
| 5,938,688 | * 8/1999 | Schiff | 607/45 |
| 6,128,538 | * 10/2000 | Fischell et al. | 607/45 |
| 6,161,045 | * 12/2000 | Fischell et al. | 607/45 |
| 6,253,109 | * 6/2001 | Gielen | 607/45 |

OTHER PUBLICATIONS

Adametz, J., Recovery of functioning in cats with rostral reticular lesions. J of Neurosurgery, 1959. (16): pp. 85–97.

Berardelli, A., Transcranial magnetic stimulation in movement disorders. Electroencephalogr Clin Neurophysiol Suppl, 1999. 51: pp. 276–280.

Cohadon, F., et al., Recovery of motor function after severe traumatic coma. Scand J Rehabil Med Suppl, 1988. 17: pp. 75–85.

Dobkin, B.H., Neuroplasticity. Key to recovery after central nervous system injury. West J Med, 1993. 159(1): pp. 56–60.

George, M.S., S.H. Lisanby, and H.A. Sackeim, Transcranial magnetic stimulation: applications in neuropsychiatry. Arch Gen Psychiatry, 1999. 56(4): pp. 300–311.

Hassler, R., et al., EEG and clinical arousal induced by bilateral long–term stimulation of pallidal systems in traumatic vigil coma. Electroencephalogr Clin Neurophysiol, 1969. 27(7): pp. 689–690.

John, E.R., The role of quantitative EEG topographic mapping or 'neurometrics' in the diagnosis of psychiatric and neurological disorders: the pros. Electroencephalogr Clin Neurophysiol, 1989. 73(1): pp. 2–4.

(List continued on next page.)

Primary Examiner—Carl Layno
(74) Attorney, Agent, or Firm—Cooper & Dunham LLP

(57) ABSTRACT

Adaptive brain stimulation systems and methods aids in the rehabilitation of patients from traumatic brain injury, coma, movement disorder, or other brain dysfunction. After a direct brain stimulator is implanted in a brain region of a patient, the patient is stimulated according to a set of stimulation parameters. A present state is measured and compared to a reference state by statistical and medically relevant criteria. The subsequent program of stimulation is dependent upon the outcome of the comparison. An adaptive brain stimulation and reinforcement system and method is also described in which a second area of the brain is stimulated when stimulation of the first brain area produces a desired effect, thereby reinforcing the prior response of the brain.

49 Claims, 6 Drawing Sheets-

OTHER PUBLICATIONS

John, E.R., et al., Quantitative electrophysiological characteristics and subtyping of schizophrenia. Biol Psychiatry, 1994. 36(12): pp. 801–826.

Kanno, T., et al., Neurostimulation of patients in vegetative status. Pacing Clin Electrophysiol, 1987. 10(1 Pt 2): pp. 207–208.

Kanno, T., et al., Effects of dorsal column spinal cord stimulation (DCS) on reversibility of neuronal function—experience of treatment for vegetative states. Pacing Clin Electrophysiol, 1989. 12(4 Pt 2): pp. 733–738.

Lee, R.H. and C.J. Heckman, Enhancement of bistability in spinal motoneurons in vivo by the noradrenergic alpha1 agonist methoxamine. J Neurophysiol, 1999. 81(5): pp. 2164–2174.

Lieber, A.L. and L.S. Prichep, Diagnosis and subtyping of depressive disorders by quantitative electroencephalography: I. Discriminant analysis of selected variables in untreated depressives. Hillside J Clin Psychiatry, 1988. 10(1): pp. 71–83.

Limousin, P., et al., Bilateral subthalamic nucleus stimulation for severe Parkinson's disease. Mov Disord, 1995. 10(5): pp. 672–674.

Limousin, P., et al., Effect of parkinsonian signs and symptoms of bilateral subthalamic nucleus stimulation. Lancet, 1995. 345(8942): pp. 91–95.

Pollak, P., et al., External and implanted pumps for apomorphine infusion in parkinsonism. Acta Neurochir Suppl, 1993. 58: pp. 48–52.

Pollak, P., et al., Long–term effects of chronic stimulation of the ventral intermediate thalamic nucleus in different types of tremor. Adv Neurol, 1993. 60: pp. 408–413.

Post, R.M., et al., Repetitive transcranial magnetic stimulation as a neuropsychiatric tool: present status and future potential. J Ect, 1999. 15(1): pp. 39–59.

Siebner, H.R., et al., Repetitive transcranial magnetic stimulation has a beneficial effect on bradykinesia in Parkinson's disease. Neuroreport, 1999. 10(3) pp. 589–594.

Sosnowski,C. and M. Ustik, Early intervention: coma stimulation in the intensive care unit. J Neurosci Nurs, 1994. 26(6): pp. 336–341.

Tsubokawa, T., et al., Deep–brain stimulation in a persistent vegetative state: follow–up results and criteria for selection of candidates. Brain Inj, 1990. 4(4): pp. 315–327.

Wood RL, W.T., Miller JL, Tierney L, Goldman L., Evaluating sensory regulation as a method to improve awareness in patients with altered states of consciousness: a pilot study. Brain Inj., 1992. 6(5): pp. 411–418.

Xue, B.G., J.D. Belluzzi, and L. Stein, In vitro reinforcement of hippocampal bursting by the cannabinoid receptor agonist (–)–CP–55, 940. Brain Res, 1993. 626(1–2): pp. 272–277.

Zihl, J., Recovery of visual functions in patients with cerebral blindness. Effect of specific practice with saccadic localization. Exp Brain Res, 1981. 44(2): pp. 159–169.

* cited by examiner

ADAPTIVE BRAIN STIMULATION METHOD AND SYSTEM

REFERENCE TO RELATED APPLICATION

This application is a continuation-in-part of parent application Ser. No. 08/596,450 filed Feb. 2, 1996, now U.S. Pat. No. 6,066,163, and hereby incorporates by reference the entire contents of the parent application.

FIELD

This patent specification relates generally to medical monitoring and medical resuscitative systems and methods. More specifically, it relates to an adaptive neural stimulator system and method for the treatment of traumatic brain injury and the often resulting persistent vegetative state or "coma," and to the treatment of other brain dysfunctions such as movement disorders, and psychiatric disorders such as depression, schizophrenia, and anxiety disorders. The system stimulates and modifies parameters of stimulation based upon the outcome of comparing the patient's present state with a reference state with the intention of improving the overall functional state of the patient. The stimulation can be electrical, pharmacological, or both.

BACKGROUND

The term "coma" is used to describe a human patient's state wherein the patient is unconscious and immobile and does not respond to intense sensory stimuli, for example, yelling. A "deep coma" occurs when this state lasts for more than 1 week. Although coma may result from several causes including drug reactions or cardiovascular stroke, it is often due to head injury, for example, head trauma due to an automobile accident.

Historically, recovery from coma has been demonstrated primarily in laboratory animals. Early studies in cats showed that functional disconnection of the reticular formation from the rest of the central nervous system (CNS) resulted in a loss of consciousness, implicating this region as responsible for the state of CNS arousal. Subsequent research (Adametz J H, Recovery of functioning in cats with rostral reticular lesions, J of Neurosurgery, 1959 (16), p. 85–97) showed that if the reticular region was destroyed in consecutive steps, rather than all at once, and the brain was given the opportunity to reorganize itself, the animals would not lose consciousness. A characteristic of the brain that enables it to respond to the insult that resulted in coma is neural plasticity which occurs when the functions of a damaged region of neural tissue is taken over by other areas that normally did not previously play a role in that particular function. Some patients are able to regain consciousness after being in a coma because the brain can respond to traumatic injury by using such adaptive capacities as functional and structural reorganization, upregulation or downregulation of a neural response to an event, and the establishment of new functional and structural connections by means of collateral sprouting and compensatory synaptogenesis.

Recent evidence indicates that direct electrical stimulation of the human brain can be effective in the reversal of persistent vegetative state (PVS) resulting from traumatic injury or stroke (Hassler R, et al., EEG and clinical arousal induced by bilateral long-term stimulation of pallidal systems in traumatic vigil coma. Electroencephalogr Clin Neurophysiol. 1969 September; 27(7): 689–690. Cohadon F, et al, Deep cerebral stimulation in patients with post-traumatic vegetative state. Neurochirurgie. 1993; 39(5): 281–292. Deliac P, et al., Electrophysiological development under thalamic stimulation of post-traumatic persistent vegetative states. Neurochirurgie. 1993; 39(5): 293–303. Cohadon F, et al., Recovery of motor function after severe traumatic coma. Scand J Rehabil Med Suppl. 1988; 17: 75–85. Kanno T, et al. Effects of dorsal column spinal cord stimulation (DCS) on reversibility of neuronal function—experience of treatment for vegetative states. Pacing Clin Electrophysiol. 1989 April; 12(4 Pt 2): 733–738. Kanno T, et al Neurostimulation for patients in vegetative status. Pacing Clin Electrophysiol. 1987 January; 10(1 Pt 2): 207–208. Tsubokawa T, et al. Deep-brain stimulation in a persistent vegetative state: follow-up results and criteria for selection of candidates. Brain Inj. 1990 October; 4(4): 315–327. Katayama Y, et al. Coma induced by cholinergic activation of a restricted region in the pontine reticular formation—a model of reversible forms of coma. Neurol Med Chir (Tokyo). 1986 January; 26(1): 1–10.) or in improving motor control in patients with movement disorders such as Parkinson's Disease (Limousin P, et al., Effect of parkinsonian signs and symptoms of bilateral subthalamic nucleus stimulation. Lancet. Jan. 14, 1995; 345(8942): 91–95. Limousin P, et al Bilateral subthalamic nucleus stimulation for severe Parkinson's disease. Mov Disord. 1995 September; 10(5): 672–674. Pollak P, et al., External and implanted pumps for apomorphine infusion in parkinsonism. Acta Neurochir Suppl (Wien). 1993; 58: 48–52. Pollak P, et al., Long-term effects of chronic stimulation of the ventral intermediate thalamic nucleus in different types of tremor. Adv Neurol. 1993; 60: 408–413.). There is also evidence that electrophysiological (EEG or ERP), electromyographic (EMG), neurochemical (CSF metabolites), peripheral (circulating beta-endorphin levels), radiological (CT scan, MRI) and clinical (Pupillary Light Reflex, Glasgow Coma Scale) measures may aid in providing useful selection criteria for patients who may be likely to successfully respond to direct brain stimulation (DBS) treatment. These measures may also offer ways to monitor the efficiency of acute or chronic DBS treatment. Since there are perhaps 2,000,000 cases of traumatic brain injury each year in the United States, with a substantial percentage leading to a persistent vegetative state or "coma", successful coma treatment would be of significant clinical utility, decreasing mortality and morbidity.

Instruments for direct electrical brain stimulation are currently available from several companies (Medtronic, Neuromed, Cochlear Corp, Advanced Bionics). These devices are in clinical use and often rely on systems chronically implanted into the brain or peripheral sites. U.S. Pat. No. 4,735,204 (referred to herein as "the '204 patent") discusses a system for controlling a neural stimulation device that is implanted in the epidural space along the spine and is used to block ascending pain signals in chronic pain. The amount of pain may change over time depending upon the patient's activity level or position, and the '204 patent discusses how the level of current supplied to an implanted stimulation electrode is modified, within certain acceptable limits, through the use of externally applied magnetic signals, thereby avoiding a visit to a medical facility. In the '204 patent the optimal level of stimulation is chosen by the patient by a criterion where the patient again attains comfort. U.S. Pat. No. 5,342,409 discusses a chronically implanted position responsive neurostimulator which is useful in the treatment of cases with chronic intractable pain, various movement disorders, and lack of bowel and bladder control, and in which the stimulation parameters are programmed into a stimulation controller by professional personnel via transcutaneous RF telemetry signals. U.S. Pat. No. 4,592, 359 discusses a multi-channel implantable neural stimulator which functions as an auditory prosthesis. The proposed system includes a transmitter and a chronically implantable receiver and an efficient transmitted data format which both transmits data and induces a charge on the implanted stimulator. U.S. Pat. No. 5,716,377 ('377 patent), discusses a method of treating movement disorders by brain stimulation which is based upon an algorithm in which a control signal is used to increase or decrease neurostimulation parameters within a predetermined range of safety. The '377 patent does not teach a method of individually changing neurostimulation parameters such as is possible using a multiple lead stimulator. Further, the '377 method and system rely on a tremor/no tremor criteria, rather than computing a score and/or storing a score, such as a Z-score, discriminant probability, or multivariate index, in order to compare different amounts of tremor which may be below a target threshold. All sensed data which indicate that the current state of the patient is below a certain threshold are treated as equal.

While the technology discussed above can be of considerable medical utility, none of the described approaches utilizes a systematic, statistical, and medically meaningful method for determining the stimulation parameters in order to optimize efficacy of stimuli to be ultimately used in treatment. Accordingly, an object of the adaptive brain stimulation (ABS) system and method disclosed in this patent specification is to greatly improve the treatment of central nervous system pathology by relying on statistically significant and medically meaningful criteria for choosing and modifying as needed a specified program of simulation.

A further object of the system and method disclosed herein is to utilize an ABS that controls multiple stimulation devices that are implanted in more than one brain region (e.g., a first brain region and a second brain region), and which stimulate these regions according to a set of parameters that produce functional or structural recovery which enables the patient to overcome unwanted effects resulting from traumatic brain injury, stroke, or other brain disorder or dysfunction. The brain stimulation may be pharmacological, electrical, or both, as described in greater detail below.

SUMMARY

In one exemplary and non-limiting embodiment disclosed herein, an adaptive brain stimulation system and method aid in the rehabilitation of patients with traumatic brain injury which has resulted in a persistent vegetative state, or other brain dysfunction. After a direct brain stimulator is implanted in a brain region of a patient, the patient is stimulated according to a set of stimulation parameters. A present state is measured and compared to a reference state. If the comparison meets a set of criteria, then the stimulation is producing a desired effect and a positive outcome is said to have occurred resulting in a continuation of stimulation according to a current or similar set of stimulation parameters. If, however, after a specified amount of time or number of attempts, the comparison fails to meet a set of criteria then new sets of stimulation parameters are selected and subsequently tested until a positive outcome occurs.

In an alternative embodiment, in the case of a positive outcome a second set of DBS's which is at another brain region may also be stimulated by a specified reinforcement schedule. If this second brain region is related to reward, then the brain is reinforced for producing a response that succeeds in meeting a criteria. There is a substantial body of literature on classical and operant conditioning that discusses such positive reinforcement.

The ABS system comprises a feedback loop that provides stimulation to a patient based upon statistical and medical criteria. In actual practice the system includes electronics, sources of power, amplifiers, stimulators, and appropriate connection and communication between functionally related components. External components can be under control of a personal computer (PC), and internal components are controlled by micro-electronics. As known in the art, and as described in the above cited material, current technology can allow the ABS system to be almost completely implanted or it may have a relatively large number of its components located external to the patient. If the ABS is located internally, it can contain both communication circuits for sending and receiving signals to its external components and a long-lasting replaceable or rechargeable power supply which can be recharged via induction or by radio frequency transmission. Since the ABS system is a medical device, it should meet patient safety standards by including protection of the patient from electrical surges and runaway feedback, and can includes the necessary hardware and software subroutines to perform appropriate diagnostic checks to ensure correct functioning.

After the patient regains consciousness by returning from the coma or manifests another desired improvement by recovering from a dysfunctional state, the ABS system can be implanted into a patient, or remain implanted, and aid in the subsequent maintenance of the normal state.

BRIEF DESCRIPTION OF THE DRAWING

For the purpose of illustrating the system and method disclosed herein, the accompanying drawing illustrates exemplary embodiments that are currently preferred; it being understood that the invention is not intended to be limited to these examples, and wherein.

DETAILED DESCRIPTION OF THE PREFERRED EMBODIMENTS

SYSTEM SPECIFICATION

Figure 1:
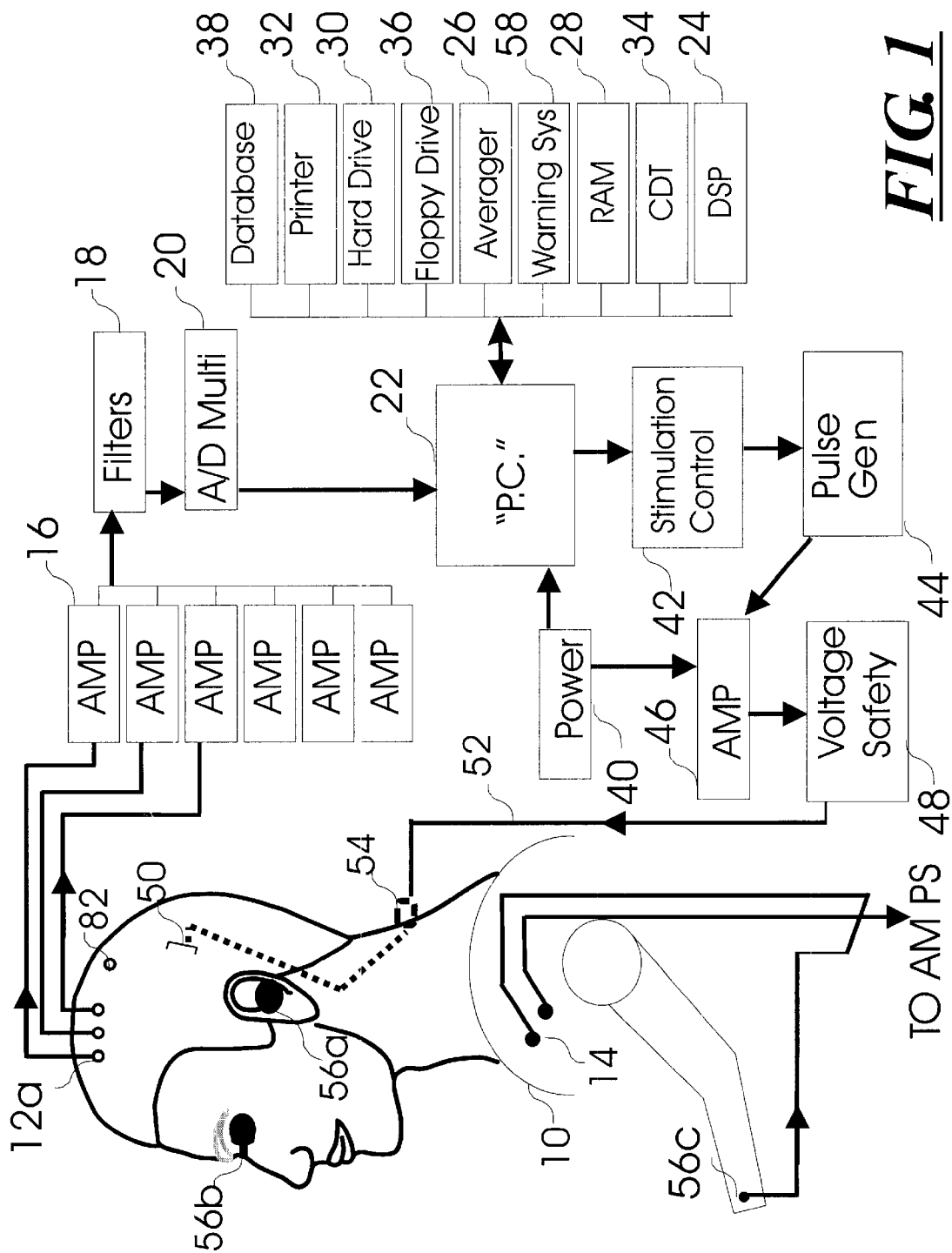
FIG. 1 is a functional block diagram illustrating a preferred embodiment.

Referring to FIG. 1, an exemplary embodiment of an ABS system includes an electrophysiological monitor that measures signals from the brain or body of a patient 10 (e.g., EEG, EKG,EP, and/or EMG signals) using EEG sensors 12a, EKG sensors 14, or EMG or other sensors (not shown), and conventional monitoring system components including amplifiers 16, filters 18, and an analogue-to-digital converter/multiplexer (A/D multi) 20. Components 15–20 can be incorporated into a circuit board that is removably inserted on the motherboard of personal computer (PC) 22. PC 22 contains known hardware such as a digital signal processor (DSP) 24 and an averager 26, or the software equivalent thereof, and suitable software, so that the digitized values of the electrophysiological signals ("the data") can be analyzed in both the time and frequency domain. Both the raw and analyzed data are collected from the patient and stored in RAM 28 according to the normal operational needs and uses of the system. Data are stored on the hard drive 30 for long term storage. The raw and analyzed data can also be outputted to a printer 32, a display device such as a computer display terminal (CDT) 34, or a conventional storage device such as a floppy disk drive 36. The attending medical personnel can use the computer's keyboard and function keys (not shown) to modify the display of the data and the stimulation parameters and stimulation treatment routines according to the desires and judgment of the attending medical personnel.

When the data are collected, they are compared to a set of reference values from a database 38 which contains a set of reference values that can include values previously obtained from the patient, values that the medical personnel have chosen, values from an appropriate normal population, or values derived from a combination of sources. The ABS disclosed herein then selects a set of stimulation parameters based upon this comparison and sends these parameters to a stimulation system. The stimulation system, which can be incorporated into and under control of the PC, includes a medically approved power source/power transformer 40, a stimulation control device 42 that guides the stimulation according to a set of stimulation parameters, and a pulse generator 44, operating under the direction of stimulation control device 42, that generates an electrical pulse train. The pulse train is sent through an output amplifier 46 and then a safety voltage control circuit 48 before it is delivered to the implanted direct brain stimulator (DBS) lead system 50. The control circuit is electrically connected to the DBS by medically approved insulated conducting wires 52 and connection plugs or other signal transmitting devices 54 arranged to form a functional transdermal electrical connection.

Instead of using a physical transdermal connection, one or more internally implanted DBS units can be programmed by and/or powered from external sources, for example by magnetic induction or radio-frequency charged super capacitors. Additionally, the components that measure and compare the present state with a reference state can be incorporated into implanted microelectronics and the recording electrodes may be placed in the dura, in/on the skull, in the brain, or in/on tissue such as muscle.

In an embodiment of the ABS system and method that can be used to treat coma in non-ambulatory patients, there are devices for auditory stimulation such as headphones 56a, for visual stimulation such as LED goggles 56b, and for somatosensory stimulation such as a tactile stimulator 56c attached to the wrist or fingers of the subject. All these, and/or any other stimulation devices, are controlled and powered by the PC. These stimulation devices enable the generation of auditory, visual, somatosensory, and/or other transient evoked potentials and steady state potentials that can be recorded from the EEG or other electrodes.

When used in the treatment of coma, the ABS also monitors autonomic nervous system measures (such as one or more of EKG, ECG, blood pressure, etc.) to detect positive effects of stimulation as well as to ensure that the stimulation is not adversely affecting vital functions. If a comparison of vital signs with stored reference values indicates that the patient has become adversely affected, then stimulation is halted and a warning system 58 alerts attending medical personnel.

ELECTRODE IMPLANTATION AND SETTING STIMULATION PARAMETERS

The stimulation should be directed at appropriately selected brain regions such as thalamic nuclei, including the center median or the intralaminar nuclei, the subthalamic nucleus or striatal structures, the dorsal columns, or selected regions of the spinal cord that project to appropriate reticular, thalamic, and cortical areas as has been described by the literature. Implantation of the stimulation devices can include a diagnostic phase in which cortical or subcortical areas are stimulated by the medical personnel and sites which produce desired changes (e.g., increases) in electrical activity, autonomic indices, or CNS metabolism can be selected as potential sites of stimulation. Appropriate sites of activation can be determined in several steps by functional and structural imaging technology such as PET, FMRI, SPECT, EEG, EP, MEG, and by pharmacological testing such as assays of CSF fluid metabolite levels, or by stimulating different areas of the brain during surgery required to implant the ABS system (MRI and FMRI might not be appropriate after the ABS system was implanted if undesirable magnetic interaction results). Since EEG and/or MEG are currently the least expensive techniques appropriate for monitoring the overall state of the CNS on an ongoing basis, they are the suitable measures to be used as indicators of CNS state during the treatment process in disorders such as coma or psychiatric disorders. Subsequent periodic diagnostic checks may be accomplished by medical personnel at various times during the treatment and the use of any of the above mentioned imaging technologies.

After the stimulation device or devices are implanted, medical personnel can determine several stimulation parameters that result in improvement in the condition of the patient. These stimulation parameters include those discussed in U.S. Pat. Nos. 4,702,254 and 4,592,359, and include pulse amplitude or current, pulse width, pulse time, pulse frequency, pulse train duration, rate of stimulation, as well as other parameters such as inter-train interval, pulse shape, DC offset, bursting or non-bursting mode, and AM or FM stimulation mode. After advantageous stimulation parameters have been determined or discovered, these can be programmed into the stimulator control. Advantageous stimulation parameters are those which cause a desired shift in the present state compared to a reference state. The ABS is also able to function in an "automatic stimulation search and selection" mode, in which stimulation parameter combinations are automatically chosen and tested in a regular or psuedo-random manner and parameters that cause an improvement in the patients condition are stored as a set of possible alternative parameters.

1. TREATMENT METHOD WITH A SINGLE BRAIN STIMULATOR

After a first set of parameters is chosen by any of the described automatic or manual methods or by a combination of the two methods, the device is set to begin a stimulation regimen.

Figure 2:
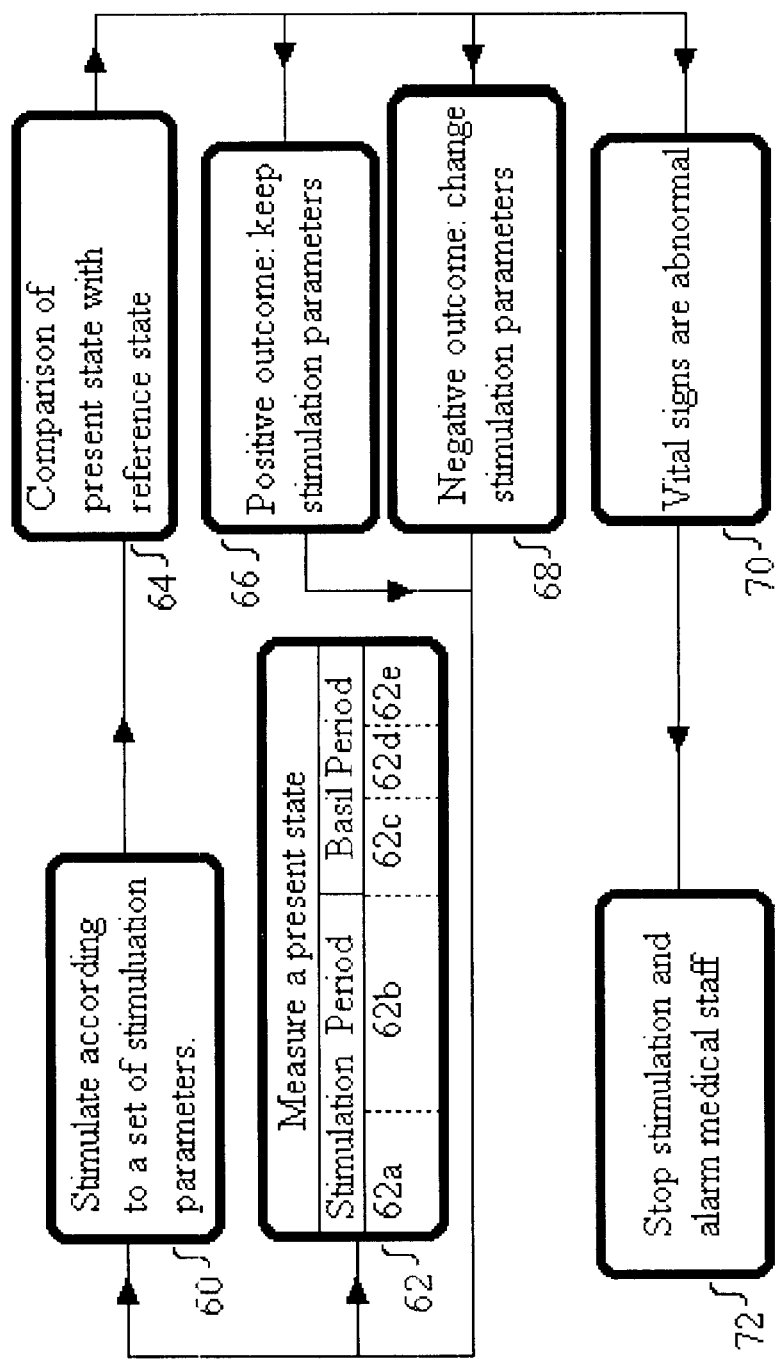
FIG. 2 illustrates an adaptive brain stimulation method, showing a way to modify the stimulation so that the patient receives safe and effective treatment.

As illustrated in FIG. 2, the first stimulation 60 occurs and the state of the subject is measured 62. The current state (a "state" is defined as a set of measures obtained from the patient 62), is then compared to a reference state at 64. The reference state may be a past state or a weighted set of past states, a normative mean value of such signals for an appropriate age matched population, possibly taking medical condition and other relevant factors such as medications into account, or a set of values chosen by medical personnel. The reference state can be some combination of such values. The comparison can lead to either a positive outcome subroutine 66 or negative outcome subroutine 68. A positive outcome results when the current state meets a set of criteria, indicating an improvement of the patient's condition, e.g., the clinical signs or monitored state indicate that the patient's brain state is moving toward a target state. When a positive outcome occurs, the set of stimulation parameters is not changed and stimulation is repeated.

If after a specified interval or number of stimulations the current state fails to meet the comparison criteria relative to a reference state, then the comparison at 64 determines that a negative outcome has occurred. In the case of a negative outcome, or several repetitions of a negative outcome in order to ensure that it did not occur by chance, the stimulation parameters are changed. Another stimulation is carried out with the changed parameters, and the present state is again compared to a reference state, until the comparison at 64 indicates that favorable mode of stimulation has again been achieved, or some other course of action is taken. For example, another change is stimulation parameter can be made, or stimulation can be discontinued by a decision of the medical personnel or by a preset timeout based on time or number or kind of stimulations. In the case of a negative outcome, the selection of subsequent stimulus parameters can be based upon a specific program of stimulation. It can be based upon a program that relies on a methodical permutation of increasing or decreasing sets of values. It can be based upon an algorithm that utilizes past successful parameters and discriminates against unsuccessful parameters for that subject, or upon values in a database based on a normative population, or upon a random or quasi-random strategy, or some other decision of medical personnel.

The ABS method and system can include monitoring of vital functions (EKG, blood pressure, respiration, etc.) to detect positive effects of stimulation as well as to ensure that vital functions are not adversely affected by brain stimulation. If a current program of stimulation begins to affect vital signs adversely, as detected at 70, stimulation is discontinued at 72 until medical personnel evaluates the medical state of the patient and decides on a new program of stimulation, if any.

A present state of a patient can be divided into a "stimulation period" and a "post-stimulus period." The stimulation period is defined as a period that is in, or is temporally close to, the period in which stimulation occurs, for example from stimulation onset until stimulation offset or lasting up to, for example, 1 second post-stimulus, as determined at 62c. The stimulation period may also be sub-divided into two or more smaller sections of interest such as 62a, 62b. The "post-stimulus period" may similarly be a single period or may be divided into two or more sub-periods such as 62c, 62d, 62e which begin after the stimulation period and last until the next stimulation period. The post-stimulus period may be characterized by complete cessation of stimulation or by a relatively decreased level of stimulation compared to the stimulatory state, or by different stimuli. Stimulation may also be continuous. Comparison of the current state with a reference state may entail a comparison of a current state concurrent with an ongoing DBS or the subsequent post-stimulus period or a fraction of that interval relative to an appropriate reference period. When the neural response to the stimulation is sufficiently large, the present state during the stimulation period can be measured even by scalp EEG electrodes. Since the ABS system can apply a discrete electrical pulse train to the brain, it should be understood by those skilled in the art that when the present state contains a sufficiently large phase-locked EEG oscillation that was elicited by the stimulation, it can be evaluated as an evoked potential with constituent components having peak amplitudes and latencies.

The comparison of the selected current state to the appropriate reference state can utilize statistical criteria which may be computed on raw measures or Z-transformed data and can include multiple t-tests to compare the mean values of the variables in each of the states, or computation of the F-ratio to compare the variance of variables in each of the states, or computation of an appropriate multivariate measure.

For example, the variance $\sigma^2$ of any variable x can be written as $\sigma^2(x)=(\Sigma x^2/n)-(\Sigma x/n)^2$ where n equals the number of measurements. The distribution of amplitudes at any frequency in the EEG is understood to be Gaussian, with a mean value equal to zero, therefore $(\Sigma x/n)^2 \cong 0$. Thus, the variance of the EEG at any frequency can be considered to be simply $\sigma^2(x)=(\Sigma x^2/n)$, in other words, equal to the mean power. The ratio of the power, ($P_T$), in any test period to the power, ($P_C$), in a reference or control period will be $P_T/P_C = \sigma_T^2/\sigma_C^2$. This expression can be treated as an F ratio yielded by a one way analysis of variance, with degrees of freedom $(a-1) \cdot n$, where a=the number of conditions compared and n=the number of measurements. This F value can be converted to a measurement of probability by using the Fischer Z transform. (In order to achieve a Gaussian distribution, the values of power can be log transformed prior to computation of the Z-score.)

In view of the above explanation, it is seen that the effect of brain stimulation upon any measurement of power in the frequency domain of the EEG power spectrum, or upon the power in any latency interval of an EP analysis epoch, can be evaluated statistically by using a ratio of powers: the ration of the power at a specified time after a period of brain stimulation, ($P_A$), to the power during a reference state, before stimulation, ($P_B$). Since normative population data, ($P_N$), at any age are available, for both the resting EEG power spectrum (e.g., as collected from scalp electrodes) as well as the EP waveshape to somatosensory or auditory stimulation across the latency epoch, the estimate of the statistical probability that a given type of stimulation has altered the EEG or the EP can be assessed in order to ascertain whether the brain of a patient displays an EEG or EP which is more normal after than before the occurrence of stimulation. That is, if $(P_N/P_A)<(P_N/P_B)$, then the brain state after stimulation is closer to the normal state than the state that was present before stimulation. (The criterion used in this expression is that the power of the reference measure in the normal state is expected to be greater than in the patient, as would usually be the case for the alpha or beta band in coma. Were delta or theta used as the criterion variable in the treatment of coma, the sign of the inequality would reverse.) $P_N$ may also be based on the value of a parameter of the EEG or a component or latency interval of the EP that the medical personnel have selected as a goal, or optimum value to be reached by that patient, or which is a self-norm of the subject during a desired state that was previously identified.

These criteria can be applied in the multivariate case. Multivariate composites or Mahalanobis distances, taking into account the covariance among several measures may also be thus assessed. A multivariate criteria can be computed using the equation $\Sigma C_i(P_{iN}/P_{iA})<\Sigma C_i(P_{iN}/P_{iB})$, where each $P_i$ is a quantitative measure of data that is obtained from any of the set of electrodes (e.g., alpha power at posterior sites, or power of an EP at a specified latency interval), $C_i$ is an appropriately chosen weighting coefficient, and the appropriate transformations are done so that the inequality is medically meaningful (e.g., a negative one (−1), or $1/P_i$ is used when appropriate). The choice of using a value other than 1 for any $C_i$ is often made based upon medically relevant criteria as will be described.

Alternatively, since the mean values, M, and the standard deviations, σ, of the power in the resting EEG are known for the delta (1.5–3.5 Hz), theta (3.5–7.5 Hz), alpha (7.5–12.5 Hz) and beta (12.5–20 Hz) bands at every scalp electrode position in the International 10/20 System for normal individuals at any age, the values of Z can be calculated for each of these frequency bands, where Z=[M−P]/σ and M=normal mean values for the age of the patient, P=patient values of present state, σ=standard deviation of the normal distribution. Improvement after stimulation or infusion, as in case of coma, may be defined as decreased positive values of Z for delta and/or theta (diminution of excesses) and decreased negative values of Z for alpha and/or beta (diminution of deficits). M and σ can also be calculated for a quantitative measure (e.g. mean alpha power) or a set of measures (e.g. alpha/theta at electrode P3 +alpha/theta at electrode P4) that are computed from physiological data collected from the patient prior to stimulation or during an alternatively defined baseline period, and changes in Z can be evaluated relative to the changes desired by the attending medical personnel or from a database constructed from previous positive outcomes. Similar to the EEG analysis, evaluation can also be carried out for the power in the epochs between, for example, 0.5 and 6.0 milliseconds of the averaged brainstem auditory evoked potentials to clicks and between 1 and 14, between 14 and 22 and between 22 and 50 ms of the averaged evoked potential to dorsal spinal column or thalamic stimulation, or stimuli delivered to the median or ulnar nerve at the wrist. Increased power in those latency intervals after stimulation indicates better transmission of sensory information to the higher structures of the brain.

Although normally only a few electrode leads (either scalp or implanted) will be used in treatment, a large set of leads may be used during the early stages of treatment (especially in the treatment of coma). Z can be made multivariate using the equation $\Sigma \underline{C}_{ik} \cdot \underline{Z}_{ik}$, where $\underline{Z}$ is a matrix of Z scores comprised of i rows for each electrode, k columns for each parameter computed on the data obtained at that electrode, and C is a matrix of coefficients that corresponds to the elements in Z. In order to decrease the size of $\underline{Z}$ and reduce the amount of redundant data contained within that matrix, M and σ can also be computed across a reference set of samples for factor scores of factors that are obtained from a principle component analysis (PCA) of, for example, spatial (EEG) or spatial-temporal (EP) data that is recorded from all the electrodes on the head (e.g., PCA may be computed across the head for EEG measures such as relative power, coherence, or power at a given latency in the case of an EP). In this case the medically meaningful Z index may be obtained by computing the deviation $Z^* = C_i |\Sigma Z_i^2|^{1/2}$, where Z* is the length of the n-dimensional vector of factor Z-scores, and $C_i$ are the corresponding weighting coefficients. Since PCA performed on data from a present state would produce a different set of factors than if the PCA were computed on data from a reference state, the factor Z-scores for the reference state and the present state should be based upon the factors generated from reference state data.

Because $C_i$ is medically relevant, it can be automatically changed during the course of the day according to the circadian changes in a patient. Further, Z may also be computed for various other biological processes that are sensed by a set of sensors implanted in or attached to the patient, such as movement or EMG sensors in the case of a Parkinsonian tremor, or measures obtained from implanted electrodes, etc. Z may also be computed on subjective measures such as pain or discomfort. During a period of subjective assessment, the patient provides subjective ratings along, for example, at least one 10 point scale where 1 and 10 are at opposite ends along some scale of sensation (e.g., pain-lack of pain, alert-drowsy, focused-dizzy).

A series of relevant publications and patents naming Dr. E Roy John as an author or inventor relate to the field of EEG "neurometrics", which evaluates Quantitative EEG measurements relative to normative data. Generally, a subject's analog brain waves at the microvolt level are amplified, separated from artifacts caused by non-brain sources of electrical activity, and converted to digital data. The data are then analyzed in a computer system to extract numerical descriptors that are compared to a set of norms which can be either the subject's own prior data (self-norm) or can be a group of normal subjects of the same age (population norm). Such an analysis can quantify any deviation of the activity of any brain region from normal values.

A computer system instrument that is based on these principles can be the "Spectrum 32" (Cadwell Instruments, Washington). That instrument is not designed for adaptive brain stimulation because it is not configured to obtain signals from implanted sensors and is not configured to provide stimulation to the patient based upon a set of criteria. Some of the aforementioned patents related to neurometrics and the Spectrum 32 are U.S. Pat. Nos. 4,279,258; 4,846,190; 4,913,160; 5,083,571 and 5,287,859. The measurements or estimates of power and other parameters discussed herein, and the mathematical operations set forth herein, can be carried out by a PC using commercially available software such as FFT (Fast Fourier Transform) software and software for carrying out specified mathematical operations on data.

If one EEG electrode is used by the ABS system and is placed at a preferred electrode site such as "Cz" according to the International 10–20 system of electrode placement, then at least one of the following variables is used in the computation of a present state: absolute or relative power in the conventionally defined delta, theta, alpha, and beta frequency bands, or a set of user specified bands. When additional pairs of homologous electrode locations are used from the right and left hemispheres of head (e.g.,F3 vs. F4 and P3 vs. P4), then measures of left-right and anterior-posterior correlation or coherence are also available to be used in the computation of the present state.

In addition to EEG, evoked responses (EP's) can be generated by means of sensory stimulation and used to guide neurostimulation in the case of disorders such as coma. Automatic detection and evaluation of EP's can be accomplished by many statistical methods. For example, digital filtering, peak detection and latency estimates, or measures of spectral power in a latency interval can be compared to normative distributions, values obtained earlier from the patient, or other appropriate reference set. Significant changes in the shape of the EP's can be automatically measured by collecting a series of single EP's and performing a Principle Component Analysis on the data which yields a series of eigenvectors that account for independent sources of variance in the data. By evaluation of the factor scores or weighting coefficients required to reconstruct the EP, the ABS can automatically detect changes in the EP. Alternatively, as known to those in the art, automatic EP software for a PC will find the amplitude, latency, or power of an EP or averaged EP, so that evaluation of the data by a trained operator is not necessary.

2. TREATMENT MODE WITH MULTIPLE STIMULATOR LEADS

Figure 3:
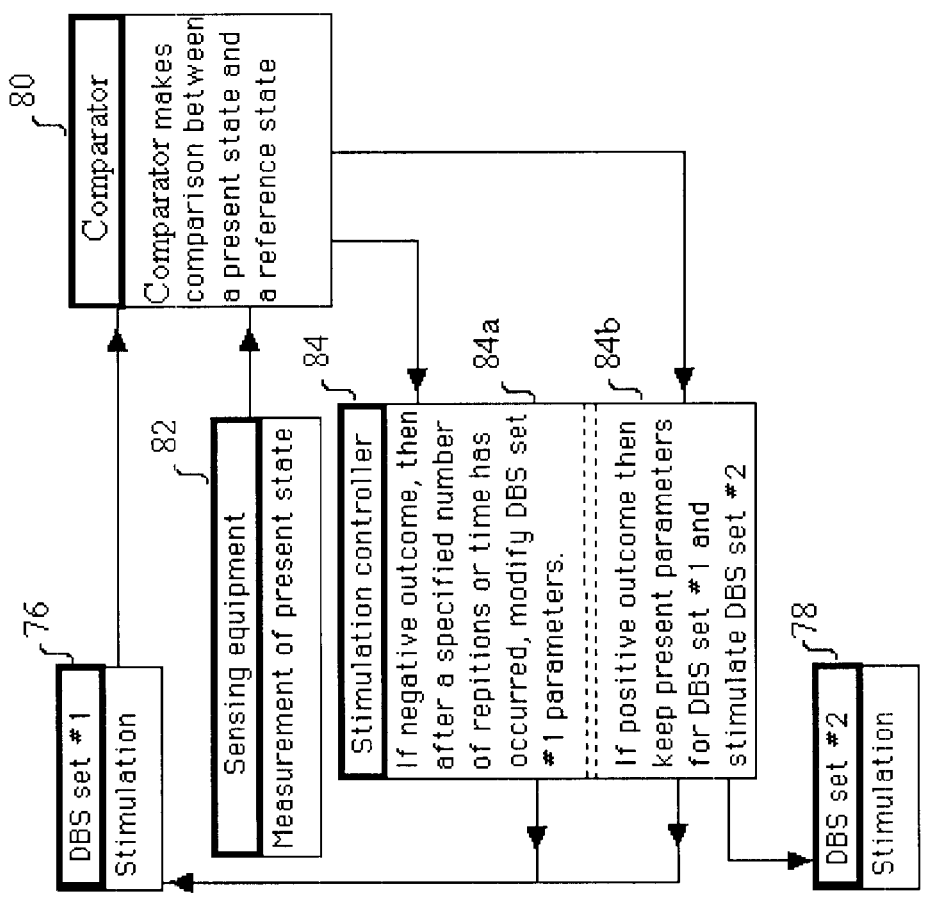
FIG. 3 illustrates an adaptive brain stimulation system and method in which two brain regions are involved in the treatment.

The treatment of brain dysfunctions or disorders such as coma, stroke, or epilepsy, or movement disorders by the ABS system can further be enhanced by incorporating an approach that includes multiple brain regions. The stimulation of multiple brain regions can be important since changes in one region may results in compensatory responses by another region. In a further embodiment of the ABS system and method, at least two stimulation sites are utilized to achieve beneficial effects, as illustrated in FIG. 3. As seen in the figure, stimulation set #1 at 76 contains at least 1 DBS device which stimulates a first brain region. Additionally, a second brain area is stimulated by stimulation set #2 at 78, which also contains at least 1 DBS device. The parameters of stimulation set #1 are determined by evaluation at a comparator 80, which makes a comparison of a present state in relation to a chosen reference state. In one embodiment, which is appropriate for the treatment of coma, an external computer and power system is used. The present state is estimated using values measured by at least one sensor 82, which is implanted and maintains electrical connectivity by means of a connection arrangement 54, or which is a scalp electrode 12a (as in FIG. 1). After the activation of stimulation set #1, two classes of stimulation cycles may occur. In one case, called cycle #1, the patient's present state fails to meet a specified criterion relative to a reference state, even after a specified time interval or number of repetitions. When cycle #1 occurs, as determined at 84a, new parameters are selected by the stimulation controller 84 and stimulation of DBS set #1 is repeated.

In another case, called cycle #2, as determined at 84b stimulation of DBS set #1 causes the patient's present state to meet specified criteria relative to a reference state. In this case, within a pre-determined time (e.g., number of milliseconds) after a positive outcome of the comparison, a paired stimulus is delivered by DBS set #2 to a second brain region according to a specified set of parameters that control the stimulation of DBS set #2. This reinforcement by DBS #2 may be regular or aperiodic. The pairing between DBS #1 and DBS #2 at 78 continues until DBS#1 fails to produce the desired results and cycle #1 again occurs. The stimulation parameters that are used on DBS set #2 can be modified to create the optimal desired neural effect by relying upon the search methods previously described for the ABS system and method, used with a single brain region.

Figure 4:
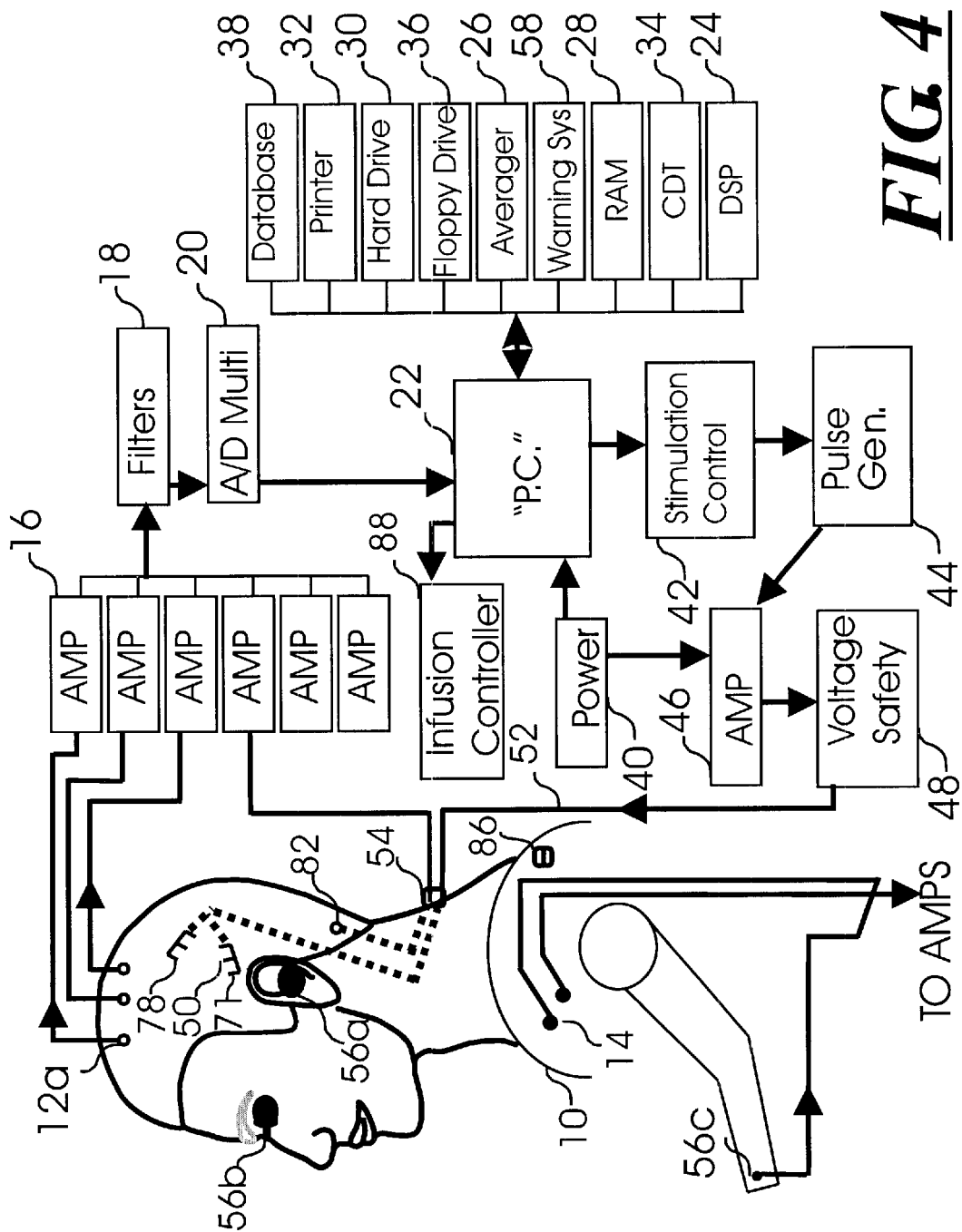
FIG. 4 is a functional block diagram illustrating an adaptive brain stimulation system and method in which two brain regions (DBS #2) are incorporated into the treatment.

FIG. 4 includes the components found in FIG. 1 as well as several additional features. In addition to a scalp electrode 12a, an implanted sensor, which can be a specialized implantable recording electrode 82, is shown. Sensor 82 obtains physiological data that is sent to PC 22 and used in the computation of a present or reference state. The single DBS 50 is now a part of DBS set #1 illustrated at 71, which contains multiple DBS's. DBS set #2, illustrated at 78, also contains several DBS's that may be used on multiple areas of the central nervous systems. In DBS set #1 and DBS set #2, electrical stimulation can be replaced by, or work in conjunction with, pharmacological stimulation achieved by a reservoir and infusion apparatus (R.I.A) 86 and infusion controller 88. In one embodiment, the infusion controller can be configured to act as a reservoir when physically connected to the R.I.A. In the illustrated embodiment, the infusion controller 88 communicates with the RIA by telemetry such as is done in the case of implantable microinfusion pumps that dispense insulin. The R.I.A. can provide a supply of pharamacological agents such as psychostimulants that can move the brain or an area of the brain into a more active state, or provide a supply of therapeutic agents such as neurotropic substances that will work either independently or in conjunction with the electrical stimulation to produce beneficial results. The substances can be stored in a distal location and transported to effective sites by means of a canal system or microcatheter system. For example, when used with a catheter in laboratory research, ALZET™ osmotic micro-pumps have delivered agents into the venous or arterial circulation, or target delivery to specific tissues or organs. ALZET™ pumps have been used to infuse agents into the brain. Targeted delivery techniques allow drug levels to be maintained locally, ensuring that effective levels are maintained in the desired target tissue. Targeted infusion can minimize unwanted systemic effects distant from the site of action. Microinfusion pumps small enough to fit on a silicon chip are presently being designed, and local injection of these substances by intracraneal or pericraneal microinfusion pumps is a preferred embodiment. The Alzet Brain Infusion Kit™ by ALZA corp. can be used in some instances. Implantable pumps currently only have about a 1 month reservoir; for more prolonged delivery, pumps may be serially implanted with no ill effects, until longer-lasting supplies are developed. Osmotic pumps offer many advantages, but the currently known models release their contents at a constant rate. Therefore, in the case of non-continuous pharmacological stimulation, a control arrangement may be used. The RIA and related infusion control can be a completely implanted device, or the RIA can maintain functional connectivity through connection plugs 54 to an infusion controller 88, which can be powered by and maintain communication with the PC 22.

Figure 7:
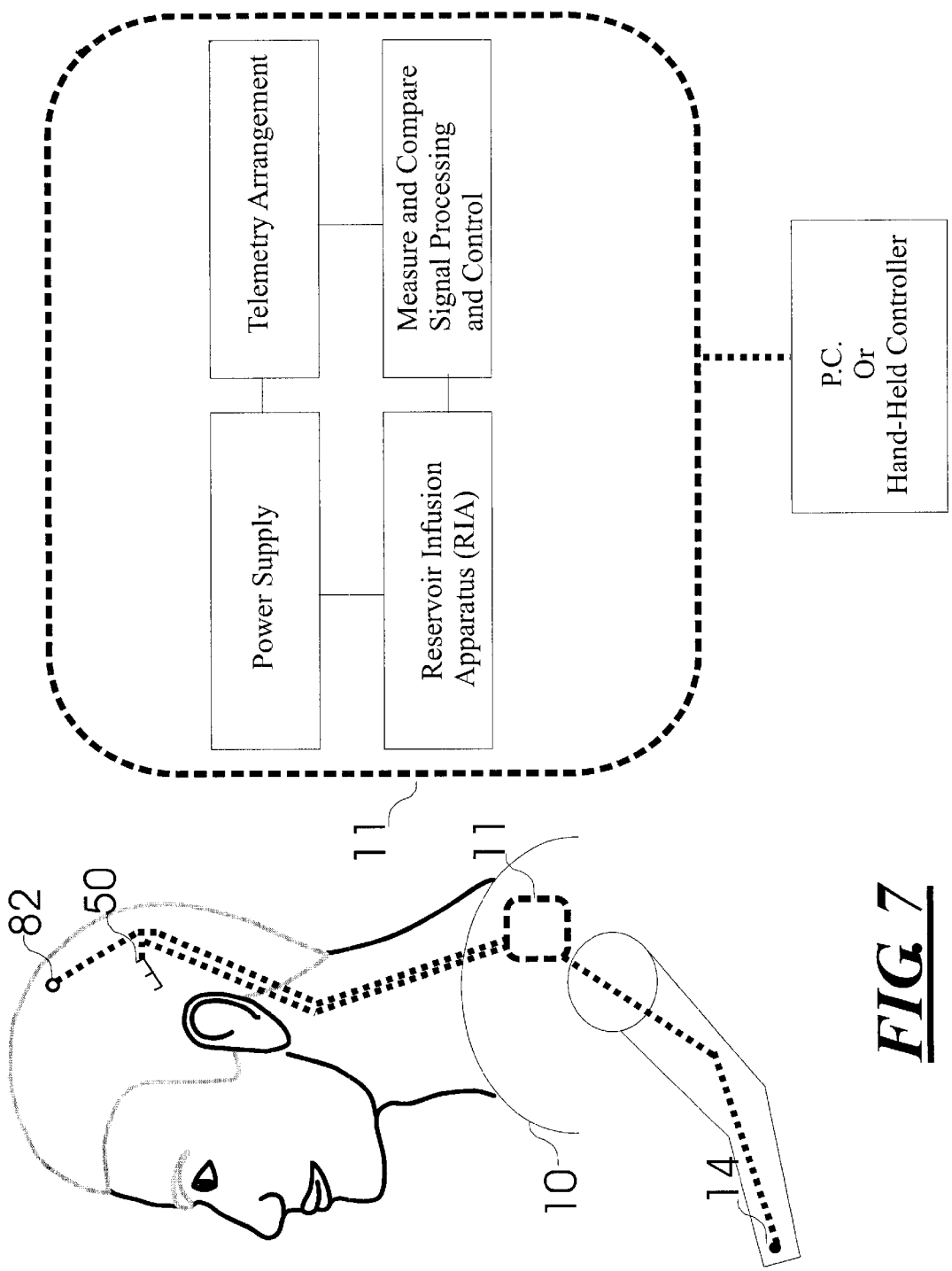
FIG. 7 illustrates an example in which the ABS (adaptive brain stimulator) is implanted.

FIG. 7 illustrates an example of an implanted adaptive brain stimulation (ABS) device 11, implanted at a suitable, medically appropriate site in a patient 10. As earlier noted and as illustrated in FIG. 7, implanted device 11 can incorporate a power supply to power the implanted components, a telemetry arrangement to enable the implanted portion to transmit information to an external processor and also to act as a receiver communicating with a portable, hand-held device, measure and compare signal processing components and control to compare the present state with a reference stat and use the results appropriately for adaptive brain stimulation, and a reservoir infusion apparatus (RIA), all interconnected to serve their purpose. External functions such as further control, storage, further processing, and others, can be carried out by an external personal computer (P.C.) or a hand-held device.

If DBS set #2 is located in an area of the central nervous system related to the non-specific reward system, then by stimulating DBS set #2 just after the occurrence of a desired present state the CNS is rewarded for generating a desired brain response. Several lines of evidence, which have appeared in reports in the relevant medical and scientific literature and which are known to those skilled in the art, indicate that contingent stimulation of the dopamine (DA) system can reinforce a particular pattern of neuronal firing that occurred previously. Paired DA reinforcement reliably elicits a multitude of desired responses from an organism and excitation of the meso-limbic DA system is functionally identical with reinforcement in classical behavioral and neurophysiologial models. For example, laboratory animals will choose to press levers instead of eating, even to the point of starvation, when lever presses are rewarded by an injection of DA directly into the brain. Further, on a cellular level, there is evidence (Olds J. Hypothalamic Substrates of Reward. Physiological Review, 42: 554–604, 1962) that biofeedback which involves DBS or microinjection of a region appropriate neurotransmitter in such brain regions as the ventral tegmental area, the hypothalamus, or nucleus accumbens, can successfully increase the frequency and/or intensity of any arbitrary reinforced event or behavior which can be controlled by the brain. By stimulating the release of a neurotransmitter or of afferent input when the brain activity of a present state yields a desirable outcome relative to a reference state, the ABS system and method can reinforce the brain for entering a desired state or, on a local level, emitting a desired electrophysiolical response (Xue B G, Belluzzi J D, Stein L (1993) In vitro reinforcement of hippocampal bursting by the cannabinoid receptor agonist (−)-CP-55,940. Brain Res. 626(1–2):272–7.

When DBS set #2 is located in an area of the central nervous system not related to the non-specific reward system, pairing DBS #1 and DBS#2 still produces beneficial effects. Paired stimulation of separate brain regions strengthens connections between these regions. The fact that appropriately paired stimulation increases and reinforces both functional and structural connectivity between the stimulated brain regions is the basis of several neurophysiological models of long term potentiation (LTP), which is the neural process assumed to be essential for storage of memory (Kandel and Schwartz, 1993). LTP was originally shown in the hippocampus, and has since been shown to occur in many other regions of the brain. Stimulation of a neuroanatomical circuit also aids in brain compensation for a traumatic injury, which includes collateral sprouting, compensatory synaptogenesis, and cortical reorganization.

When trauma causes injury or destruction to a region of the CNS, the brain can reorganize ineffective or severed pathways as adjacent areas develop new connections. Compensatory responses occur both more readily and more rapidly with stimulation of relevant brain areas. Patients who have lost their ability to walk showed recovery from this injury by reorganizing CNS connections rostral to brainstem, but only when they were forced to practice walking on a specialized treadmill (Dobkin B H., Neuroplasticity. Key to recovery after central nervous system injury. West J Med. July 1993; 159(1): 56–60.). Practice has also been shown to be crucial to recovery of function in patients with cortical blindness (Zihl J. Recovery of visual functions in patients with cerebral blindness. Effect of specific practice with saccadic localization. Exp Brain Res. 1981; 44(2): 159–169.).

In coma, the opportunity for stimulation-assisted compensatory responses by the CNS is diminished because the brain is in a relatively inactive state. By concurrently stimulating two or more areas of the brain such as the reticular system and the thalamus, or the motor cortex and sensory or association areas (John, Mechanisms of Memory, 1967) the functional connection between these 2 regions can be strengthened. Further, in addition to contiguity, by concurrent stimulation including a reward region, such as the nucleus accumbens, the brain might enhance communication between any two regions.

DBS set #1 may be only one DBS device. In an alternative embodiment, DBS set #1 may include multiple DBS's, each of which may be governed by an independent set of stimulation parameters including onset and offset times. The stimulation parameters can include relative latency or polarity values, where the "latency" of a given DBS is defined in relation to a separate DBS. The DBS's will usually be bipolar in structure, having a relative anode and cathode between which the current travels, and can be concentric bipolar electrodes because these are designed to optimally stimulate a specific region. Separate DBS's can be given alternating and opposite relative polarities so that current travels between them and creates a more diffuse field of activation.

One advantage of using multiple stimulation devices is that several areas that send afferents to a target brain region can be stimulated simultaneously or in sequence, increasing the probability of activation of a target area. An alternative method of using a DBS set with multiple stimulators uses stimulators at various sites along a functional neuroanatomical circuit. These DBS's can be stimulated at relative latencies that would approximate or "mimic" normal neural transmission along the circuit.

DBS's can consist of implanted electrodes or stimulating devices which may be active or passive and which may be connected to distal devices or may be entirely self-contained. Further, instead of electrical stimulation, stimulation can utilize pharmacological means such as systemic injection or local microinjection of psychostimulants (amphetamine) or other functional agonists or antagonists which can be routed directly into a specific brain area or into a lateral ventricle. The injectable mediums can be stored at a distal site adjacent to other implantable devices and can be connected to the release site by a subcutaneous canal system. The release of the substance can be under the control of a central processor containing the required analytical electronics and a storing, pumping, or other dispensing means. Further, substances such as psychostimulants can be introduced into the patients by intravenous infusion, direct application to the nasal mucosa, or by infusion of the substance into the lateral ventricle, such as from an Ommaya sack reservoir before a period of electrical stimulation, increasing the likelihood of CNS response. Diffusion from a stored receptacle such as an Ommaya reservoir can be through a canal system that relies on passive diffusion, or the flow may be more strictly regulated in terms of time and amount of released material by micro-pump systems and control arrangement that can be located external to the CNS or to the patient, and in communication with the comparator.

Additionally, both electrical and pharmacological stimulation can be used together to further improve the patients condition. In one application, infusion of a substance intrinsically excitatory to a particular region is made contingent upon a specific pattern of cellular firing or upon an increase of a specific frequency in the EEG. Local administration of a neurotransmitter contingent upon a particular firing pattern increases the chances for subsequent repetition of this pattern. Thus, linking the infusion of a region-appropriate neurotransmitter such as norepinephrine into the reticular region to a state of increased excitability should facilitate the probability of an increase in subsequent firing rates.

Stimulation parameters can also include conditional criteria, the result of a logical operation performed upon a condition that results in a positive or negative outcome. As with the previously disclosed statistical and medically relevant criteria, in the case of conditional criteria only when a positive outcome occurs does stimulation take place. Additionally, like the other parameters, conditional criteria may be set independently for different stimulators. Conditional criteria are additional parameters such as time since last stimulation, time of day, etc., and can be designed so that stimulation occurs only at certain stimulators under specified conditions. Conditional criteria may be advantageous for several reasons. For example, if the comparison between a present state and a reference state yields a sustained positive outcome and DBS stimulation set #2 is located in nucleus accumbens, then continuous stimulation of this area could lead to long term elevated neurotransmitter levels (such as DA) and receptor desensitization. By including a conditional criterion that requires a specified amount of time to have elapsed since the last stimulation, problems such as receptor desensitization are avoided. Alternatively, conditional criteria can be set so that if repeated periods of stimulation have recently occurred, subsequent additional stimulation will occur only when the comparison of present state with reference state is more than an relatively larger pre-selected or incremental value.

Additionally, during the period of treatment, measures such as temperature can provide a way of detecting either regular or irregular occurrences of circadian or ultradian rhythmicity. In certain cases of coma, a detectable sleep/wake cycle does exist. If such cycles approximate natural circadian rhythmicity, then the conditional parameters can be set so that stimulation occurs only during the more active state. Stimulation can be set to reinforce present or emerging circadian cycles and not to occur during an inappropriate chronobiological state, such as periods which might suggest sleep or less active states.

When brain or body state is measured in a multi-sensor embodiment of the ABS, analysis of measures used to define the present state can include analysis in the time domain, such as correlation or covariation between sensors. Analysis of measures can entail automated or manual evaluation of the components of the specific neural response to the stimulation known as an evoked potential (EP). The analysis of the EEG or EP data may be in the time or the frequency domain and can include measures of absolute power, relative power, mean frequency, symmetry or coherence, for a specified conventional frequency bands or a set of user defined bands or measures of waveshape or measures of power in early versus later latency intervals.

Different types of brain trauma, medical condition, or medication could produce variability in the values detected by the sensors. Therefore, a database can be provided that adjusts statistical response criteria so as to be medically meaningful. The comparison between present and past state can be modified based upon factors including: site and number of recording electrodes and stimulators, response to various stimulus parameters, medication, response selection and multiple montage criteria for various brain injuries. Supplementary to a reference database, individualized comparison criteria can be set and modified by the attending professional personnel. Medically relevant criteria are important to ensure efficient and effective treatment. For example, if a brain injury caused a lateralized bias in damage, the comparison of present state to reference state is modified so that any improvement on the less damaged side is weighted more heavily than the damaged side, as that side is more likely to recover more quickly. Without weighting the measured variables according to medically relevant criteria, a relevant change in a small region of a brain that may be detected by only one electrode might not reach significance since when its value is averaged with the other electrodes it is less likely to reach significance.

In addition to the previously described types of direct electrical brain stimulation, stimulation of all five senses, both separately and in combination, has been shown to be effective in decreasing the time spent in coma (Sosnowski C, et al. Early intervention: coma stimulation in the intensive care unit. J Neurosci Nurs. December 1994; 26(6): 336–341; Mitchell S, et al. Coma arousal procedure: a therapeutic intervention in the treatment of head injury. Brain Inj. July 1990; 4(3): 273–279. Wood R L, et al. Evaluating sensory regulation as a method to improve awareness in patients with altered states of consciousness: a pilot study. Brain Inj. September 1992; 6(5): 411–418). Sensory stimulation achieves excitation of such areas as the reticular formation, lemniscal pathways, specific and non-specific and cortical regions. Using the ABS, sensory stimulation parameters including intensity, duration, and frequency can be modified and the corresponding resultant present state compared to a reference state in order to choose the optimum stimulation parameters for creating cortical excitation. Sensory stimulation may be combined with DBS's to maximize induced arousal by stimulating the brain in two different ways.

Currently, the brainstem auditory evoked potential (BAEP) and somatosensory evoked potential (SSEP) are considered valuable diagnostic means to determine the probability that a patient will successfully recover from coma and regain consciousness. By defining a present state, estimated by qualifying the BAEP, SSEP, EEG or EMG during the post-stimulus period, and comparing it to an appropriate reference state, the clinical efficacy of a set of parameters for peripheral stimuli can be evaluated and changed if necessary to aid in recovery of patients from coma.

Additionally, the ABS system and method disclosed herein can be used in the treatment of sensory disorders by sensory aids that stimulate the CNS or sensory pathway, such as a multi-channel implantable neural stimulator which functions as an auditory prosthesis. By comparing the present EP to a sensory input to a reference EP obtained from a past sensory input the stimulation parameters of an implanted device can be set to achieve the optimum performance from the implanted stimulator.

3. TREATMENT METHODS AND STRATEGIES

In addition to the treatment of coma as earlier described, the ABS system and method disclosed herein can be used in the treatment of movement disorders such as those found in Parkinson's Disease. The treatment can be by direct stimulation of the CNS, where the present state is computed primarily from EMG data and is compared to a reference state. The stimulation parameters are changed according to the result of this comparison so that the stimulation parameters ultimately used are of greatest benefit to a patient as is now described. These techniques can also be applied in the treatment of rigidity, spasticity, dystonia, and other movement disorders.

3.1.a ABS in the Treatment of Tremor

In one preferred embodiment, the method and system of the adaptive neurostimulation system may be used in the treatment of tremor. A sensor, such as an electrode, is placed in a limb, for example the left arm. A baseline state, representing the tremor activity with no therapeutic DBS, is obtained and a measure of the tremor. For example, the magnitude the tremor is computed from an appropriately filtered EMG signal (see next paragraph). If the tremor occurs over a range of frequencies, then a combined index (for example, an average) of different frequencies can be computed (from the relevant spectral components of power spectra of the signal) and used as a measurement of tremor. The frequency (or frequencies) at which the tremor occurs can be decided by medical personnel who examine the frequency content of processed EMG activity during a baseline period in which the patient shows signs of tremor. These "tremor frequencies" can then and programmed into the neurostimulation system so that it may measure the appropriate spectral components.

As known, the magnitude of the tremor can then be computed from the sensed data using several conventional techniques such as:

1. An FFT algorithm that can produce an estimate of power over the frequency range of the tremor, or an estimate of power of the total EMG, which can be used in the computation of EMG variance (for F-ratio).
2. A digital and programmable bandpass filter algorithm with the passband centered at the frequency of the tremor and the magnitude computed as the average deviation from zero over time, or
3. Using a template to which the incoming EMG activity, or a transform of the activity (such as the rectified signal after it has been band pass or low pass filtered), is matched. The sensed data may be filtered before being compared to a template for reduction of background activity which may be in the very low frequency range (e.g., <1 Hz) or higher frequency range (e.g., >50 Hz)

3.1.b Obtaining Initial Stimulation Parameters

In order to obtain a baseline estimate of the tremor activity, (N) of samples of EMG data are obtained, with each sample lasting a short time (T), for example 5 seconds. For example, if 60 samples are obtained (N=60), each lasting 5 seconds (T=5 sec.), with the inter-sampling-interval (ISI) lasting 55 seconds, then 60 samples will be taken over an hour long period for a total of 300 seconds (N*T), or 5 minutes of data. If the ISI is reduced towards 0, the time required to obtain a baseline can be as short as 3–5 minutes. It is likely that at least 1 minute of data may be needed for a stable estimate of the average magnitude of the tremor. In the case of an FFT analysis, each one-second duration of data can be submitted to the FFT in order to provide a frequency estimation with 1 Hz resolution. The mean and standard deviation (Std) of the 300 estimates of the magnitude of the tremor can be computed. A baseline estimate can be obtained during a period in which no DBS occurs or, alternatively, during DBS. The lack of DBS occurs during a "stimulation off" or S1 state, while the "stimulation on" or S2 state indicates that DBS is occurring.

Values obtained during the baseline, such as the average spectrum, can be transmitted to an external receiver and printed out by medical personnel in order to ensure that the sensed data make physiological sense and are of good quality. If more than one sensor is used, then Z-scores can also be computed for data from each of the sensors for the baseline condition and these values can also be transmitted to the external receiver for print out to hard copy.

In the next step DBS occurs. In this step, medical personnel adjust the initial frequency and intensity of stimulation in order to produce the maximum initial reduction of tremor. For example, the initial stimulation values may be 140 Hz for the stimulation frequency and 2 V for the stimulation voltage and the initial pulse width may be 60 microseconds. (Alternatively, the intensity of the stimulation may be specified by constant current.) If several stimulation electrodes have been implanted, then all of these are initially activated. Similar to the baseline condition, an assessment of tremor magnitude for the stimulation "on" state (S2) can be assessed over a period such as 1 hour to obtain the measures of mean, Std, Z-score, and mean power spectra.

3.1.C Start of Treatment

As in the case of manual adjustment of neurostimulation parameters, during adaptive adjustment of the stimulation parameters only changes within acceptable limits are permitted. In a conventional non-adaptive neurostimulator, the stimulation parameters may be adjusted upwards (by a physician) if the tremor returns or may be lowered due to the emergence of side effects which disturb the implantee. Normally, the voltage may be adjusted by medical personnel over a range of +/−2 volts within the initial settings, but should remain below 3–5V because a higher level of stimulation is more likely to cause side effects or even injury to the patient. Accordingly, medical personnel program the initial stimulation settings and acceptably safe range for the adaptive stimulation. In the next step, the adaptive stimulation begins, with the goal to minimize the amount of neurostimulation used while still inhibiting the emergence of tremor.

Figure 5:
FIG. 5 is a graph illustrating evaluation of tremor activity based upon a baseline state.
Figure 6:
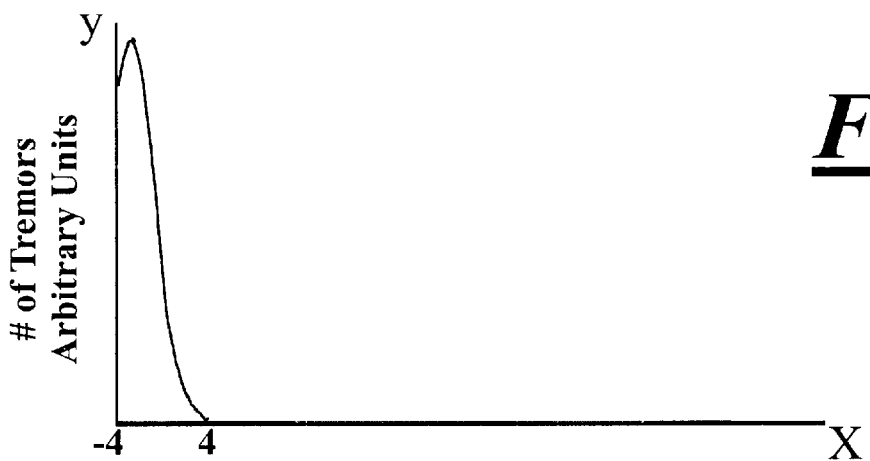
FIG. 6 is a graph illustrating a distribution of tremor activity during stimulation.

FIGS. 5 and 6 illustrate two different ways of scoring the amount of tremor present at any given time. In FIG. 5 the amount of tremor is evaluated based upon the amount of tremor present in a stimulation "off" baseline state. Referring to FIG. 5, tremor activity can be measured during a baseline "reference tremor" condition and in order to obtain the mean and standard deviation values for a stimulation "off" condition. During stimulation the amount of tremor can then be scored according to the mean and standard deviation of the baseline condition. For example, during stimulation the tremor scores should be around −2 to 4 most of the time. In this case the effect of the stimulation is defined somewhat upon the mean and variance of the baseline state. When multiple indices are used, these values can be converted into Z-scores and the maximum or average z-scores can be used to evaluate the amount of tremor present.

In FIG. 6, the amount of tremor is evaluated based upon the variance of the tremor during a S2 baseline state. Tremor activity may be highly skewed, where the decreases in the amount of tremor from the mean level of tremor are much less than the increases. The skewed distribution may be normalized to a Gaussian by a log transform. Z-scores may then be validly computed. Order statistics may also be used, in the case where log transforms are inappropriate, such as utilizing the cumulative probability distribution function for the individual's reference state (Zar J H. Biostatistical analysis. $4^{th}$ ed. Upper Saddle River, N. J.: Prentice-Hall, 1999; p27; p72–73; p96–98; p147–150; p165, e.g, Wilcoxon paired-sample test when more than one sample of sensed data are compared to a reference state; p475–477). Alternatively, standard deviations could be calculated and then multiplied by a set of weighting coefficients that account for the skewed distribution. Z-scores may also be computed in the case of multiple sensors. The choice of baseline discussed in connection with FIG. 6 may be more appropriate in the subsequent detection of the emergence of tremor and is the type of baseline that would be achieved, for example, using a reference baseline state that was periodically updated by windowing the data, where the reference baseline Z-scale is updated over time (e.g. $X_t$ is the current value and $X_{t-1}$ to $X_{t-21}$ is the data window representing the last 20 values in time). Additionally, aside from Z-scores there are other systems that could be used in evaluating changes in the amount of tremor and which might rely on the use of a quartile system, absolute or relative amounts of change, the computation of the F-ratio based upon the magnitude of the response between the S1 and S2 states, etc. Tables 1–4 are set forth and discussed below to illustrate simulated examples. In Tables 1–3, the baseline was obtained during the stimulation "on" state. Accordingly, most of the types of stimulation tested produce insignificant increases or decreases in the amount of tremor, and only a few stimulation combinations produce significant Z-Scores. The Z-Scores in the table may represent an average of the Z-scores of several consecutive and independent samples of sensed data. In the case where the baseline was obtained during the stimulation "off" state most of the Z-Scores would likely be negative and significant (e.g., above 1.96 in the negative direction, i.e., below −1.96

Adaptive Stimulation Algorithm #1

| Stimulation Electrode | Voltage | 1 | 2 | 3 | 4 | Tremor Z-score |
|---|---|---|---|---|---|---|
| Trial 1 | 3 V | 40 | 40 | 40 | 40 | 0.1 |
| Trial 2 | 3 V | 38 | 38 | 38 | 38 | 0.5 |
| Trial 3 | 3 V | 36 | 36 | 36 | 36 | −1.5 |
| Trial 4 | 3 V | 34 | 34 | 34 | 34 | 1 |
| Trial 5 | 2 V | 40 | 40 | 40 | 40 | 0.5 |
| Trial 6 | 2 V | 38 | 38 | 38 | 38 | 0.1 |
| Trial 7 | 2 V | 36 | 36 | 36 | 36 | 2 |
| Trial 8 | Cancelled | Cancelled | Cancelled | Cancelled | Cancelled | Cancelled |
| Trial 9 | 1 V | 40 | 40 | 40 | 40 | 3 |
| Trial 10 | Cancelled | Cancelled | Cancelled | Cancelled | Cancelled | Cancelled |
| Trial 11 | Cancelled | Cancelled | Cancelled | Cancelled | Cancelled | Cancelled |
| Trial 12 | Cancelled | Cancelled | Cancelled | Cancelled | Cancelled | Cancelled |

Table 1: Frequency Sweep Range 40–34, 2 Hz Steps: All Electrodes

In this method the frequency of stimulation of all four stimulation electrodes is decreased at the same time. The tremor Z-score is computed at each rate. Using 36 Hz at 3 volts seems to produce the greatest reduction in tremor, while this rate is less optimal when 2 volts are used. When the Z-score is above 2, the tremor is reasonably present and testing of that particular parameter is aborted. In addition to changes in voltages, the inter-pulse interval, pulse duration, pulse polarity, pulse-train duration, duty cycle, current, etc. can be tested at each repetition rate.

Adaptive Stimulation Algorithm #2

| Stimulation Electrode | Voltage | 1 | 2 | 3 | 4 | Tremor Z-score |
|---|---|---|---|---|---|---|
| Trial 1 | 2.5 V | 40 | 40 | 40 | 40 | 0.1 |
| Trial 2 | 2.5 V | 38 | 40 | 40 | 40 | 0.5 |
| Trial 3 | 2.5 V | 36 | 40 | 40 | 40 | −0.5 |
| Trial 4 | 2.5 V | 34 | 40 | 40 | 40 | 1 |
| Trial 5 | 2.5 V | 40 | 38 | 40 | 40 | 1 |
| Trial 6 | 2.5 V | 40 | 36 | 40 | 40 | 2 |
| Trial 7 | 2.5 V | 40 | 40 | 38 | 40 | 0.2 |
| Trial 8 | 2.5 V | 40 | 40 | 36 | 40 | −1 |
| Trial 9 | 2.5 V | 40 | 40 | 34 | 40 | −1.5 |
| Trial 10 | 2.5 V | 40 | 40 | 40 | 38 | 0.7 |
| Trial 11 | 2.5 V | 40 | 40 | 40 | 36 | −0.4 |
| Trial 12 | 2.5 V | 40 | 40 | 40 | 34 | −0.4 |

Table 2: Frequency Sweep Range 40–34, 2 Hz Steps: Single Electrode Manipulation

In this method the frequency of stimulation of each of the four stimulation electrodes is decreased individually, to discover optimal parameters for each single lead stimulation. The tremor Z-score is computed at each rate. Using 34 Hz at 2.5 volts in lead 3 (while leads 1, 2, and 4 use 40 Hz) seems to produce the greatest reduction in tremor. When the Z-score is above 2, the tremor is reasonably present and testing of that particular parameter is aborted. Accordingly, in electrode 2 no data are collected using a stimulation rate below 36 Hz.

Adaptive Stimulation Algorithm #3

| Stimulation Electrode | Voltage | 1 | 2 | 3 | 4 | Tremor Z-score |
|---|---|---|---|---|---|---|
| Trial 1 | 3 V | 40 | 40 | 40 | 40 | −0.3 |
| Trial 2 | 3 V | 38 | 38 | 40 | 40 | 0.5 |
| Trial 3 | 3 V | 36 | 36 | 40 | 40 | −0.5 |
| Trial 4 | 3 V | 34 | 34 | 40 | 40 | 0.8 |
| Trial 5 | 3 V | 38 | 40 | 38 | 40 | 0.5 |
| Trial 6 | 3 V | 36 | 40 | 36 | 40 | −0.7 |
| Trial 7 | 3 V | 34 | 40 | 34 | 40 | 1 |
| Trial 8 | 3 V | 38 | 40 | 40 | 38 | 0.7 |
| Trial 9 | 3 V | 36 | 40 | 40 | 36 | 2 |
| Trial 10 | 3 V | Cancelled | Cancelled | Cancelled | Cancelled | Cancelled |
| Trial 11 | 3 V | 40 | 38 | 38 | 40 | 0.1 |
| Trial 12 | 3 V | 40 | 36 | 36 | 40 | −2 |
| Trial 13 | 3 V | 40 | 34 | 34 | 40 | 0.2 |
| Trial 14 | 3 V | 40 | 40 | 38 | 38 | |
| Trial 15 | 3 V | 40 | 40 | 36 | 36 | −0.4 |

-continued

| Adaptive Stimulation Algorithm #3 | | | | | | |
|---|---|---|---|---|---|---|
| Stimulation Electrode | Voltage | 1 | 2 | 3 | 4 | Tremor Z-score |
| Trial 16 | 3 V | 40 | 40 | 34 | 34 | 0.3 |
| Trial 17 | 3 V | 40 | 38 | 34 | 38 | 2.3 |
| Trial 18 | 3 V | Cancelled | Cancelled | Cancelled | Cancelled | Cancelled |

Table #3: Frequency Sweep Range 40–34, 2 Hz Steps: Paired Electrode Combinations In this method the frequencies of stimulation of a pair of stimulation electrodes are decreased at the same time. The tremor Z-score is computed at each rate. Using 36 Hz at 3 volts again seems to produce the greatest reduction in tremor, but this is greatest when this occurs at stimulation electrodes 2 and 3. In Table 1 it can be seen that when all the electrodes are set at 36 Hz the reduction in tremor amplitude produces a Z-score of only −0.5, this can be somewhat understood from the results obtained in Trial 9 and Trial 12.

| Adaptive Stimulation Algorithm #4 | | | | | |
|---|---|---|---|---|---|
| Stimulation Electrode | 1 | 2 | 3 | 4 | Tremor Z-score |
| Trial 1 | 3 V | 3 V | 3 V | 3 V | −0.1 |
| Trial 2 | 2.8 V | 2.8 V | 2.8 V | 2.8 V | 0.2 |
| Trial 3 | 2.6 V | 2.6 V | 2.6 V | 2.6 V | 0.2 |
| Trial 4 | 2.4 V | 2.4 V | 2.4 V | 2.4 V | 0.8 |
| Trial 5 | 2.2 V | 2.2 V | 2.2 V | 2.2 V | 0.9 |
| Trial 6 | 2.0 V | 2.0 V | 2.0 V | 2.0 V | 2 |
| Trial 7 | 2.2 V | 2.2 V | 2.2 V | 2.2 V | 0.8 |
| Trial 8 | 2.0 V | 2.0 V | 2.0 V | 2.0 V | 2.2 |
| Trial 9 | 2.2 V | 2.2 V | 2.2 V | 2.2 V | 0.7 |
| Trial 10 | 2.0 V | 2.0 V | 2.0 V | 2.0 V | 2.1 |
| Trial 11 | 2.2 V | 2.2 V | 2.2 V | 2.2 V | 0.8 |
| . | | | | | |
| Trial 444 | 2.2 V | 2.2 V | 2.2 V | 2.2 V | 2.3 |
| Trial 445 | 2.4 V | 2.4 V | 2.4 V | 2.4 V | 0.8 |
| . | | | | | |
| Trial 900 | 2.2 V | 2.2 V | 2.2 V | 2.2 V | 0.6 |
| Trial 901 | 2.0 V | 2.0 V | 2.0 V | 2.0 V | 2.5 |
| Trial 902 | 2.2 V | 2.2 V | 2.2 V | 2.2 V | 0.7 |

Table #4: Voltage Sweep Range 3 to 2, 0.2V Steps: All Electrodes

In this method the voltages of stimulation of all the electrodes are decreased at the same time. The tremor Z-score is computed at each voltage level. After trial 11 the lowest voltage for stimulation is set at 2.2 volts since none of the other voltages produce a significant negative Z-score. The objective of the above procedure is to produce equivalent suppression of tremor using the least voltage (or current) possible with the assumption that the lower the voltage used, the lower the chance for side effects and the lower the energy consumption of the stimulation over time. Z-values that are within +/−1.96 are not significantly different from the reference condition at the 0.05 level. Some time later (Trial 444) the stimulation voltage fails at continuously suppressing the tremor and the voltage is increased by 0.2 volts. Since this increase halts the tremor the voltage is not increased further. This lowest voltage is periodically checked (starting some time later at Trial 900) to ensure that this voltage can not be reduced further. The failure of a lower voltage (at Trial 901) causes the voltage to remain at 2.2 volts until the next periodic check.

Adaptive stimulation may follow the strategy illustrated in Table 1, where the stimulation parameters of all four stimulation electrodes are modified concurrently. Electrodes 1–4 may be in the nucleus ventralis intermedius of the thalamus (VIM), the subthalamic nucleus (STN), the globus pallidus internus (GPi), and may all be in one structure or dispersed within these separate areas. Although stimulation often occurs at much higher frequency rates (e.g., 130 Hz), the table shows stimulation decreasing from 40 to 34 Hz. It should be understood that the principle would be the same for higher frequencies, and that the 2 Hz steps could be increased to 5 Hz steps, or beyond (likewise, when approaching an optimal setting, the steps can get smaller than 2 Hz). The other stimulation parameters such as pulse width, train duration, inter-train interval, etc are held constant over all the trials.

With regard to Table 1, during Trial 1 the 4 electrodes stimulate at 40 Hz, using a voltage of 3V and a Z-Score of 0.1 is obtained (Z was not zero due to noise). In Trial 2 the frequency of stimulation is decreased by 2 Hz to 38 Hz and the Z-Score is increased to 0.5. In trial 3, however, there is a slight decrease in Z-score which indicates that a reduction in tremor occurred. In trial 4, the Z-score increases suggesting that 34 Hz is too low. In Trial 5 the voltage is decreased and the series of frequencies is tested again. However, during this test the Z-Score increases to 2, which means that the tremor has increased, and further decreases in the value of that parameter are aborted at that voltage range. At 1 volt the testing is halted after 1 trial. This method can then be used with other stimulation parameters such as pulse width. If this procedure is done during an evaluation period under the direction of medical personnel, then this entire procedure can be repeated 3 times and the results can be sent to an external device for printout in order to enable medical personnel to set the correct initial stimulation values. If these results occurred during treatment rather than during an initial evaluation period, then the adaptive stimulator would choose to use 36 Hz at all electrodes. This method can be termed the multiple DBS iterative (MDBSI) technique.

Table 2 illustrates a similar set of hypothetical results for single electrode manipulations. The frequency of stimulation is decreased on an individual basis and the tremor Z-Score is computed at each rate. The intent, in part, is to discern the contribution of each electrode in the control of tremor. In certain patients, one electrode may work significantly better than the others. This method can be termed the single DBS iterative (SDBSI) technique.

Table 3 illustrates a set of results when pairs of electrodes are used. This may be a powerful technique because single stimulation sites may interact with other sites. These types of interactions would not be seen in the case where changes were made on an electrode by electrode basis or when changes were made for all electrodes at the same time. This method can be termed the paired DBS iterative (PDBSI) technique.

Once the stimulation parameters are chosen, either adaptively or by medical personnel, the daily stimulation treatment can also use adaptive stimulation. A simple strategy for adaptive treatment can be seen in Table 4. As the table shows, the voltage of all the electrodes is swept over the range of 3 to 2 Volts, decreasing in 0.2 Volt increments. In this method the stimulation voltages are simultaneously decreased. The tremor Z-score is computed at each voltage level. The Z-score may be computed as the mean value of the measurement of the present level of tremor which is occurring in the presence of stimulation $-M(S)-$ minus the mean value of the measurement during a baseline period $-M(T)-$ divided by the standard deviation of measurement made during the baseline period, STD(T):

$$Z=(M(S)-M(T))/Std(T),$$

where the measurement of tremor is EEG, EMG, or other appropriate measurement such as the output of a motion sensor, and M(T) is the mean value of the measurement of the tremor during baseline and M(S) is the mean value of the measurement of the tremor during stimulation and Std(T) is the standard deviation of the measurement of the tremor during baseline.

T may be a multivariate correlate of tremor data at a particular sensor, where each measure is multiplied by an appropriate co-efficient. In the case of disorders such as depression, where population normative values exist, then M(S) would be the individual man for a particular measure and M(T) would be the population normative mean value for that same measure.

The lowest voltage can be found using a 3 attempt rule. For example, when a decrease in voltage causes the tremor Z-Score to increase beyond +2, the probability of an increase in tremor having occurred by chance is less than 0.05 (i.e., $p<0.05$). Accordingly the decrease in the voltage is treated as unsuccessful and the voltage is again increased to the prior level. After 3 attempts, the voltage is set at the lowest successful level, which here occurs on trial 11 (see table 4). Some time later (Trial 444) the stimulation voltage fails at continuously suppressing the tremor and the voltage is again increased by 0.2 volts (auto-compensation), where it remains until a given amount of time has elapsed and the stimulator performs the next scheduled test. Since, in the example, this increase in voltage successfully reduced the tremor to acceptable levels, the voltage was not increased further in an iterative process. The stimulator may conduct these scheduled tests periodically, for example, every 24 or 48 hours (Trial 900) in order to ensure that this voltage can not be reduced further. The failure of a lower voltage (at Trial 901) causes the voltage to remain at 2.2 volts until the next periodic check because the prior 2 tests at 2.0 Volts had also failed. This strategy can be applied to the frequency of stimulation as well, or to pairs of electrodes, or single electrodes as was shown earlier.

The patient can keep a log reporting subjective experiences and sensations that occur during stimulation treatment. Medical personnel can then compare the patient log to the stimulation parameters which existed for equivalent time periods, which the neurostimulator can store and output during periodic evaluation sessions conducted by a clinician. By comparing a patient's experiences to the stimulation record, medical personnel can constrain future adaptive stimulation in a logical manner so that unwanted side effects are not experienced by the patient. For instance, if the patient only felt side effects when the stimulation at lead 4 was above a certain voltage level, then voltage at the other stimulation leads could be increased to compensate for a reduced voltage level at this lead. The adaptive stimulation method may be completely automatic, and during the treatment mode the parameters that produced, for example, the top 10% of negative Z-Scores, could be stored since these were the most successful. The neurostimulator could then use the stored successful parameters when a set of stimulation parameters no longer yielded the desired results. The set of parameters could also be set by medical personnel, based upon evaluating the patient log and the stimulation log of the ABS system.

There are many alternatives of this basic idea. In another embodiment, rather than an electrode placed in or near a muscle to collect EMG data, the sensor may be a motion sensor. In another embodiment, the electrode might be located in or near the somatosensory cortex, where EEG related to the tremor may be recorded.

Hand-held portable controllers can be provided that patients may use in order to re-initialize the stimulator to the parameters initially set by medical personnel, or to select from sets of stimulation parameters programmed in by medical personnel.

These methods provide considerable advantages over known earlier proposals. For example in U.S. Pat. No. 5,716,377 ('377 patent), a method of treating movement disorders by brain stimulation is discussed which is based upon an algorithm in which a control signal is used to increase or decrease neurostimulation parameters within a predetermined range of safety. The '377 method does not teach a method of individually changing neurostimulation parameters such as is possible using a multiple lead stimulator. Accordingly, interactions between stimulator leads (for example a pair of leads), and optimal lead combinations are not able to be found since, in the '377 method, any given parameter would be changed at all leads at the same time (in fact the '377 patent discusses the use of only a single electrode lead and does not discuss multiple lead strategies). Further, the '377 method relies on a tremor/no tremor criteria, rather than evaluating a present state by computing a score and/or storing a score, such as a Z-score, discriminant probability, or multivariate index, in order to compare different amounts of tremor. The '377 patent simply uses a target threshold criteria. All sensed data which indicate that the current state of the patient is below a certain threshold are treated as equal. Further the method discussed in the '377 patent does not provide testing of interactions between parameters since parameters are modified independently in sequence: since parameters are tested sequentially, rather than permitting sets of parameters to be modified in parallel, useful interactions, and therefore clinically successful combinations of parameters, may not be found. For example, in the ABS method and system disclosed herein, since voltage may be decreased systematically in 0.2 volt steps, and different pulse widths can be tested at each step, then the total voltage can be considered: using 2.2 volts with pulse widths of 60 microseconds could result in more voltage over time than using 2.4 volts and 20 microsecond pulses. Alternatively, if one electrode is kept at 2.8 volts while 3 others are maintained at 1.2 volts the total energy used is less than if all electrodes were set at 2.4 volts. Lower levels of stimulation may serve to save energy (particularly important for implanted power sources) and also act to reduce unwanted side effects.

Stimulation does not need to be continuous. For example, the stimulator disclosed herein may typically stimulate for 30 sec using a given set of parameters and then wait 5 min prior to stimulating again. These inter-stimulation intervals can be adjusted by medical personnel, or can be one of the parameters used in adaptive feedback. Additionally, the ABS method and system can work for the various types of motor problems such as tremors at rest as well as intention tremors.

The adaptive stimulation methods also need not be used continuously. For example, if the total amount of EMG activity is above a certain level the patient may be engaged in a highly physical activity (e.g., hammering). During this period the possibility of using adaptive feedback successfully is diminished considerably and therefore is discontinued until the EMG levels return to within an acceptable range (however, stimulation is still continued according to the last set of stimulation parameters).

The stimulator's telemetry arrangement that enables it to transmit information to an external processor can also act as a receiver. A receiver would be useful if patients are provided with a portable, hand-held device that enables them to turn the adaptive feedback operation off whereby the stimulation parameters revert to those initially set by medical personnel.

In the ABS methods described above, stimulation typically occurs according to strategies in which the brain is periodically stimulated, a present state is sensed and compared to a reference state and, if the reference state does not meet a criteria, then the stimulation is treated as unsuccessful and the parameters are changed prior to subsequent stimulation. This method uses periodically delivered stimulation, whether it is needed or not. There is evidence that brain stimulation may cause changes that are of relatively long duration. Much of this evidence comes from studies which have shown that short periods of transcranial magnetic stimulation is able to produce therapeutic effects, possibly producing physiological changes that last well beyond the period of stimulation (Post R M.(1999) Repetitive transcranial magnetic stimulation as a neuropsychiatric tool: present status and future potential. J ECT; Siebner H R.(1999) Repetitive transcranial magnetic stimulation has a beneficial effect on bradykinesia in Parkinson's disease. Neuroreport; George M S (1999). Transcranial magnetic stimulation: applications in neuropsychiatry Arch Gen Psychiatry; Klein E (1999). Therapeutic efficacy of right prefrontal slow repetitive transcranial magnetic stimulation in major depression: a double-blind controlled study Arch Gen Psychiatry, 1999; Transcranial magnetic stimulation in movement disorders. Electroencephalogr Clin Neurophysiol Suppl. 1999;51:276–80. Review.) but there is also in vivo evidence as well (Lee R H (1999) Enhancement of bistability in spinal motoneurons in vivo by the noradrenergic alphal agonist methoxamine. J Neurophysiol; 81(5); 2164–74). Accordingly, stimulation may also occur according to a strategy in which after an initial stimulation occurs the present state is periodically compared to a reference state. If a present state fails to meet a criteria then stimulation occurs. The present state is then again compared to a reference state. If the comparison again fails to meet a criteria then the stimulation parameters are iteratively changed (and stimulation occurs again) until the comparison between a current state and a reference state again succeeds in meeting criteria. In this manner stimulation is provided on an as needed basis rather than relying on a method which assumes that stimulation is needed periodically in the treatment of a given disorder.

3.2 ABS in the Treatment of Psychiatric Disorders

The methods described in sections 3.1.a and 3.1.b could be applied in the case of treating a psychiatric disorder, such as depression or schizophrenia, where the Z-score may be computed on a multivariate index (which may include Z-scores of various measures and appropriate coefficients), and where the both increases and decreases in certain types of brain activity may be sought. In addition to a multivariate Z-score, a discriminant score classification system may be used to guide the neurostimulation.

Using discriminant scores to evaluate brain state is discussed in U.S. Pat. No. 5,083,571 ('571), which is incorporated by reference herein, as well as in literature which is also herein incorporated by reference (John, E. R., Prichep, L. S., Alper, K. R., Mas, F. G., Cancro, R., Easton, P., & Sverdlov, L. (1994). Quantitative electrophysiological characteristics and subtyping of schizophrenia. *Biological Psychiatry*, 36(12), 801–826. John, E. R. (1989). The role of quantitative EEG topographic mapping or 'neurometrics' in the diagnosis of psychiatric and neurological disorders: the pros. Electroencephalography & Clinical Neurophysiology, 73(1), 2–4.Lieber, A. L., & Prichep, L. S. (1988). Diagnosis and subtyping of depressive disorders by quantitative electroencephalography: I. Discriminant analysis of selected variables in untreated depressives. Hillside Journal of Clinical Psychiatry, 10(1), 71–83).

Multivariate stepwise discriminant functions are mathematical classifier algorithms which will have different values for the a prori defined groups (or conditions, or states, etc) they were built to distinguish, for example, depressed and non-depressed states. Discriminant functions are weighted combinations of a selected subset of variables, each of which makes some independent contribution to the overall discrimination, and is optimized for maximum separation between the two conditions.

Such functions can be used to estimate the probability that the patient's abnormality profile is likely to belong to the distribution of profiles of the depressed population. Such patterns have been described in the literature for scalp recorded EEG and could be transformed for the expected changes with implanted cortical electrodes. In a similar way to that described above for tremor, one or more stimulating electrodes (or infusion leads for using pharmacological agents) can be placed such that deliveries of stimulation to those regions can be assessed for degree to which they reduce the probability of depression as estimated from the EEG sensors.

For example, in the case of depression, one or more electrodes can be implanted to record EEG. Sites would be selected using knowledge relative to the regions of scalp recorded EEG which show the most significant deviations from expected normal values in depressed patients. A baseline, eyes closed resting EEG could then be recorded in the patient and Z values for baseline obtained and submitted to a multivariate discriminant function to determine the probability that the patient is depressed. This probability function would be a continuous number from 0–100, where any number larger than 50 would be considered to reflect the probability of being depressed. The aim would be to reduce the probability, with the intent of getting the number below 50, and optimally, as low as possible, by adaptive manipulation of the stimulating parameters and regions of stimulation. Because normative data (using scalp EEG electrodes) has only been collected with eyes closed and because QEEG evaluation of state is optimal in the relaxed state with eyes closed, adaptive stimulation parameter determination can be done only once per day when a patient activates the ABS system. During this period the implantee would sit with eyes closed in a relaxed state. Alternatively, when using implanted electrodes, successful evaluation of data recorded during normal activity may be possible.

Alternately, an embodiment might be based on using stimulation to modify the degree of coherence between hemispheres, optimizing for the set of stimulating parameters and sites which "normalize" the coherence values. Baseline values for coherence can be computed and Z transformed relative to each successive trial of stimulating parameters and sites, and adaptively modified to find the one with the Z value closest to zero. (QEEG frontal incoherence is a major characteristic of depression.)

The ABS method and system disclosed herein includes several ways in which ABS may be used in the treatment of various brain disorders and dysfunctions. In its simplest form the ABS uses one sensor, one stimulation lead, and compares a present state to a reference state in order to evaluate the effectiveness of stimulation. In more extensive embodiments, several sensors and multiple electrical/pharmacological stimulators may be used. Several examples were provided in order to demonstrate how the ABS may first achieve and subsequently maintain optimal stimulation. Unlike known prior proposals, the disclosed method and system comprise statistically comparing a present state to a reference state, which may be a self norm, a population value, or a value from some other source, and which may be based upon a specific baseline period or upon baseline created from a moving temporal window of past states.

The adaptive brain stimulation system and methods described herein can be used in the treatment of a brain disorder or dysfunction which is at least impaired cognitive function, chronic pain, neuropathic pain, seizure, deficits of attention or intention or working memory or awareness, Alzheimer's disease, Dementia, psychosis, schizophrenia, drug induced psychosis or other drug induced abnormal state, an anxiety disorder, depression or other mood disorder, or is due to a brain injury produced by stroke, blunt head trauma, missile penetration, neurotoxicological agents, virus, anoxia, ischemia, nutritional deficiencies, developmental diseases, degenerative diseases, infectious diseases or complications thereof, or an abnormal brain state due to or causing drug addiction or alchoholism, or is due to a motor disorder such as tremor and the class of tremor disorders, intentional tremor, dystonia, tardive-diskenesia, ballism, spasticity, athetosis, rigidity, akinesia, bradykinesia, or other hyperkinetic or hypokinetic disorder.

The disclosed embodiments of the adaptive brain stimulation system and method are based upon three components: stimulation, comparison of a present state with a reference state, and subsequent stimulation that is contingent upon the results of the comparison. Although modifications and changes may be suggested by those skilled in the art, it is the intention of the inventor to embody within the patent warranted herein all changes and modifications as reasonably and properly come within the scope of the contribution to the art.

What is claimed is:

1. An adaptive brain stimulation system for treating a brain disorder or dysfunction of a patient comprising:
   a. one or more sensors of biological activity coupled with a patient to sense a present state of a patient;
   b. stimulating circuits coupled with the patient to stimulate a first brain region of the central nervous system of the patient according to a first set of stimulation parameters;
   c. comparator circuits coupled with the one or more sensors to receive present state data therefrom regarding the present state of the patient and to carry out a statistical comparison operation between the present state data and reference state data, said comparison operation resulting in a positive outcome or a negative outcome; and
   e. adjusting circuits coupled to the comparator circuits to receive data therefrom regarding said positive or negative outcome and coupled to the stimulating circuits to adjust the stimulation parameters according to the outcome of said comparison of the present state data and the reference state data.

2. An adaptive brain stimulation system as in claim 1 in which the one or more sensors are implanted within or are external to the patient and sense a present state data related to a measurement or set of measurements sensed during a period of active stimulation or at least one fraction of said period of active stimulation, or during a post-stimulation period, or at least a fraction of said post-stimulation period.

3. An adaptive brain stimulation system as in claim 1 in which the present state data relate to measures sensed by the sensor or set sensors implanted internally within or located externally to a patient.

4. An adaptive brain stimulation system as in claim 1 wherein the reference state data are selected from a database which contains at least one the following: a previous state of the patient, a weighted sum of previous states, a population normative value in a normal state, a stimulation "on" state, a stimulation "off" state, or under the influence of a pharmacological agent, or a weighted state computed based upon evidence of neuronal damage or other physiological, neuroanotomical, or neuropharmacological characteristics of said patient.

5. An adaptive brain stimulation system as in claim 1 wherein said comparison operation is performed between the present state data and the reference state data in the time domain or in the frequency domain, or on a transform of or fraction of said time or frequency domain, or on a user defined or calculated threshold value, or on a set of threshold values, said comparison operation using a set of statistical criteria and a set of medically meaningful weighing coefficients chosen by medical personnel or selected from said database.

6. An adaptive brain stimulation system as in claim 1 wherein the stimulating circuits comprise a DBS set #1, said DBS set #1 being comprised of at least one DBS.

7. An adaptive brain stimulation system as in claim 6 wherein DBS set #1 comprises multiple DBS's, each independently activated and subsequently independently controlled by separate ones of the stimulation parameters.

8. An adaptive brain stimulation system as in claim 1 wherein the stimulation parameters include pulse amplitude, pulse width, onset and offset times, frequency, a burst firing mode and a non-burst firing mode, AM and FM state, DC offset, output current, output voltage, relative polarity, and relative latency.

9. An adaptive brain stimulation system as in claim 1 in which the present state data are obtained when the one or more sensors are partially or fully implanted inside of the patient or located fully external to the patient.

10. An adaptive brain stimulation system as in claim 1 in which the one or more sensors include at least one of the following: an internally implanted electrode, a conventional scalp EEG electrode, a pet scanner, a spect scanner, a MRI scanner, a FMRI scanner.

11. An adaptive brain stimulation system as in claim 1 in which the stimulating circuits comprise circuits providing at least one of the following types of stimulation: electrical, magnetic, and pharmacological.

12. An adaptive brain stimulation system as in claim 1 in which the stimulating circuits provide direct stimulation or stimulation by induction.

13. An adaptive brain stimulation system as in claim 1 further including a monitoring circuits coupled with the stimulating circuits and with the patient to monitor the autonomic nervous system thereof and halt or reduce the operation of the stimulating circuits if vital signs of the patient become medically unsafe.

14. An adaptive brain stimulation system as in claim 1 in which the stimulating circuits provide at least one of the following types of stimulation: visual, auditory, and tactile sensory stimulation.

15. A method of using the neurological stimulation system of claim 1, further including detecting a present state characterized by selected rhythmic or non-rhythmic changes in one or more of the patient's temperature, eye movement, neurochemical (CSF metabolites), or neural activity, and only enabling stimulation when said rhythmic or non-rhythmic changes are detected.

16. An adaptive brain stimulation system as in claim 1 comprising a controller external to the patient and comprising power source, data memory, telemetry arrangement, display, and interface devices, said controller including said comarator and adjusting circuits and enabling patients to modify neurostimulation to re-initialize stimulation parameters to initial settings by medical personnel and to select from sets of parameters set by medical personnel and to store current parameters when they produce a subjective desired result and to choose from past stimulation parameters that achieved desired results, and to select a program of stimulation in which the parameters cycle between a number of past stimulation parameters that achieved desired subjective results or past desired comparison results, and to halt stimulation or sensing or both during rigorous activity or prior to sleep, and to halt stimulation for a desired time interval.

17. An adaptive brain stimulation system as in claim 16 in which at least a portion of said controller is contained in a hand-held device communicating wirelessly with system components implanted in the patient.

18. An adaptive brain stimulation system comprising:
   a. biological sensors coupled with a patient to sense a present state of at least a first brain region or a first set of brain regions and a second brain region or a second set of brain regions of a patient;
   b. first stimulating circuits coupled with a first brain region or a first set of brain regions of the patient by a DBS set #1 to carry out stimulation according to a first set of stimulation parameters;
   c. second stimulating circuits coupled with a second brain region or a second set of brain regions of the patient by a DBS set #2 to carry out stimulation according to a second set of stimulation parameters;
   d. a comparator coupled with the sensors to receive data related to said present state and compare the present set data with reference state data, said comparing leading to a positive outcome or a negative outcome;
   e. adjusting circuits coupled with the first and second stimulating circuits to control the first and second set of stimulation parameters according to the outcome of said comparing of the present and reference states.

19. An adaptive brain stimulation system as in claim 18 in which the sensors sense the present state during a period of active stimulation, during a post-stimulation period, or during a period that can occur in part before and in part after the period of active stimulation.

20. An adaptive brain stimulation systems as in claim 18 in which the sensors are implanted internally within the patient.

21. An adaptive brain stimulation system as in claim 18 wherein said reference state is selected to be a previous state of the patient, a weighted sum of previous states, a population normative value in a normal state, a stimulation "on" state, a stimulation "off" state, or under the influence of a pharmacological agent, or a weighted state computed based upon evidence of neuronal damage or other physiological, neuroanatomical, or neuropharmacological characteristics of the patient.

22. An adaptive brain stimulation system as in claim 18 wherein the comparator compares the present state data on a time domain or on a frequency domain, or on a transform of the frequency domain, based upon the reference state data in the same domain, or to a threshold value or to a set of threshold values, said comparison using a set of statistical criteria.

23. An adaptive brain stimulation system as in claim 18 wherein DBS set #1 comprises at least one DBS.

24. An adaptive brain stimulation system as in claim 18 wherein DBS set #1 comprises multiple DBS's each independently activated and subsequently independently controlled by different ones of the stimulation parameters.

25. An adaptive brain stimulation system as in claim 18 wherein said stimulation parameters include pulse amplitude, pulse width, onset and offset times, frequency, a burst firing mode or a non-burst firing mode, AM or FM state, DC offset, output current, output voltage, relative polarity, and relative latency.

26. A method of using adaptive brain stimulation in the treatment of brain disorder or dysfunction of a patient comprising:
   a. sensing a present state of at least one brain region;
   b. stimulating a first brain region or a first set of brain regions according to a set of stimulation parameters,
   c. performing a statistical comparison between the present state and a reference state,
   d. changing said stimulation parameters if the comparison fails to meet selected criteria, and
   e. repeating steps a, b, c, and d a number of times.

27. A method of claim 26 further including stimulating a second brain region or a second set of brain regions if the comparison meets selected criteria.

28. A method of using adaptive brain stimulation in the treatment of Parkinson's Disease and other movement disorders which comprises:
   a. sensing the present state of at least one brain region and/or peripheral region;
   b. stimulating a first brain region or a first set of brain regions according to a set of stimulation parameters;
   c. performing a statistical and medically significant comparison between the present state and a reference state;
   d. changing said stimulation parameters if the comparison fails to meet selected criteria; and
   e. repeating steps a, b, c, and d a number of times.

29. A method as in claim 28 including the step of stimulating a second brain region or a second set of brain regions if the comparison succeeds in meeting the criteria.

30. A method as in claim 28 in which the comparison includes assigning relatively large weighting coefficients to the sensing of said peripheral region, said sensing being accomplished by conventionally located EMG electrodes.

31. A method as in claim 28 in which the stimulating comprises at least one of electrical, magnetic, and pharmacological stimulation.

32. A method of claim 28 including the step of providing positive reinforcement by stimulating at least a second brain region if the comparison succeeds in meeting the criteria.

33. A method according to claim 28, wherein conditional parameters cause said stimulating to be applied continuously, intermittently as needed, or periodically.

34. A method according to claim 28, wherein the brain disorder or disfunction is at least one of impaired cognitive function, chronic pain, neuropathic pain, seizure, deficits of attention or intention or working memory or awareness, alzheimer's disease, dimentia, psychosis, schizophrenia, drug induced psychosis or other drug induced abnormal state, an anxiety disorder, depression or other mood disorder, or is due to a brain injury produced by stroke, blunt head trauma, missile penetration, neurotoxicological agents, virus, anoxia, ischemia, nutritional deficiencies, developmental diseases, degenerative diseases, infectious diseases or complications thereof, or an abnormal brain status due to or causing drug addiction or alcoholism.

35. An adaptive brain stimulation process of treating a patient comprising:
  a. stimulating a first brain region or a first set of brain regions of the patient according to a set of stimulation parameters;
  b. sensing a present state of the patient;
  c. comparing data related to the sensed present state of the patient to data related to a reference state to derive comparison results;
  d. determining whether to make a change in the stimulation parameters and, if so, what change, depending on the comparison results;
  e. making any changes in the stimulation parameters determined in the preceding step d; and
  f. repeating steps a, b, c, d, and e a number of times.

36. A process as in claim 35 including stimulating a second brain region or a second set of brain regions of the patient depending on the comparison results.

37. A process as in claim 36 in which the stimulating of a second brain region or a second set of brain regions comprises causing a positive reinforcement.

38. A process as in claim 35 in which the step of sensing a present state of the patient comprises sensing a state of one or more peripheral regions of the patient's body.

39. A process as in claim 38 in which the step of sensing comprises sensing Parkinson's tremor.

40. A process as in claim 38 in which the step of sensing comprises sensing one or more movement disorders.

41. A process as in claim 35 in the step of making changes in the stimulation parameters comprises one or more of a multiple DBS iterative (MDBSI) process, a single DBS iterative (SDBSI) process, and a paired DBS iterative (PDBSI) process.

42. A process as in claim 35 in which the step of making changes in the stimulation parameters comprises selecting stimulation parameters from a set of stored parameters used in previous stimulating steps and determined in previous comparing steps to produce desirable results.

43. An adaptive brain stimulation process of treating a brain disorder or dysfunction of a patient comprising:
  a. sensing a first present state of the patient;
  b. comparing data of the sensed present state of the patient to data from a reference state to derive comparison results;
  c. repeating steps a and b, after a specified delay, if said comparison results meet a specified criteria and performing steps d, e, f, g, h and i if said comparison results fail to meet said specified criteria;
  d. stimulating a first brain region or a first set of brain regions of the patient according to a set of stimulation parameters;
  e. sensing a second present state of the patient;
  f. comparing data related to the sensed second present state of the patient to data related to a reference state to derive comparison results;
  g. determining whether to make a change in the stimulation parameters and, if so, what change, depending on the comparison results;
  h. making any changes in the stimulation parameters determined in the preceding step g; and
  i. repeating steps a, b, and c a specified number of times.

44. An adaptive brain stimulation process of treating a brain disorder or dysfunction of a patient comprising:
  a. setting a specific value for at least one stimulation parameter and stimulating at least one brain region or set of brain regions
  b. sensing a first present state of the patient;
  c. comparing said sensed first present state of the patient to data from a reference state to derive a comparison result score;
  d. augmenting or decrementing the value of said at least one stimulation parameter
  e. repeating steps a, b, c, and d a specified number of times to obtain a set of comparison result scores
  f. setting said at least one stimulation parameter to said value that resulted in the lowest comparison result score of said set of comparison result scores
  g. sensing a specified number of times to obtain a number of discrete samples of a second present state
  h. comparing each of said discrete samples of a second present state or the mean of said discrete samples of a said present state to a reference state in order to obtain a success score, and performing step i if said success score fails to meet a specified criteria and repeating steps g and h if said success score succeeds in meeting said specified criteria.
  i. repeating steps a, b, c, d, e, f, g and h.

45. An adaptive brain stimulation process of treating a brain disorder or dysfunction of a patient as described in claim 44, wherein step a comprises setting a specific value for at least one stimulation parameter to affect at least one pair of neurostimulation leads.

46. An adaptive brain stimulation process of treating a brain disorder or dysfunction of a patient as described in claim 44, wherein step f comprises comparing all the said result scores, and in the case where two or more result scores are within a specified proximity to each other, the stimulation parameter that resulted in the lowest amount of a specified stimulation parameter is selected.

47. An adaptive brain stimulation process of treating a brain disorder or dysfunction of a patient as described in claim 44, where step h comprises comparing each of said discrete samples of a second present state or the mean of said discrete samples of a said present state to a reference state in order to obtain a success score, and if said success score fails to meet a specified criteria, entails referencing a database and replacing at least one value of a stimulation parameter with a value that was selected in the past due to producing a desired result score, and repeating steps g and h prior to accomplishing step i.

48. A method of using adaptive brain stimulation for treating a patient using the paired DBS iterative (PDBSI) process comprising:

a. stimulating a first brain region or a first set of brain regions of the patient according to a set of stimulation parameters;

b. sensing a present state of the patient;

c. comparing data related to the sensed present state of the patient to data related to a reference state to derive comparison results;

d. determining whether to make a change in at least one of said stimulation parameters for two stimulation electrodes and, if so, what change, depending on the comparison results;

e. making any changes in the stimulation parameters determined in the preceding step d; and f. waiting a specified amount of time and then repeating steps a, b, c, d and e for a specified number of times g. adjusting the stimulation parameters to the settings which produced the lowest said comparison results or the highest said comparison results h. repeating steps a, b, c, and h, while said comparison results of step c succeed in meeting some specified criteria and if said comparison results fail to meet said specified criteria, repeating steps a, b, c, d, e, f, g and h.

49. An adaptive brain stimulation process of treating a patient comprising as described in claim 48, wherein step b comprises sensing a present state data of the patient and performing signal analysis on said data and if said signal analysis indicates that said patient is sleeping, and if sleeping has been defined as a conditional criteria, then waiting a specified delay and performing step b again.

* * * * *